United States Patent [19]

Chappell et al.

[11] Patent Number: 5,723,087
[45] Date of Patent: Mar. 3, 1998

[54] WEB MATERIALS EXHIBITING ELASTIC-LIKE BEHAVIOR

[75] Inventors: Charles W. Chappell, West Chester; Eugene R. Sorensen, Sharonville; Kenneth B. Buell, Cincinnati; John J. Curro, Cincinnati; Michele A. Mansfield, Cincinnati, all of Ohio

[73] Assignee: The Procter & Gamble Company, Cincinnati, Ohio

[21] Appl. No.: 692,986

[22] Filed: Aug. 7, 1996

Related U.S. Application Data

[60] Continuation of Ser. No. 566,203, Dec. 1, 1995, abandoned, which is a division of Ser. No. 203,087, Feb. 28, 1994, Pat. No. 5,518,801, which is a continuation-in-part of Ser. No. 100,958, Aug. 3, 1993, abandoned.

[51] Int. Cl.⁶ .................................................. B29C 49/00
[52] U.S. Cl. ........................ 264/284; 264/280; 264/282
[58] Field of Search ............................ 264/239, 280, 264/282, 283, 284

[56] References Cited

U.S. PATENT DOCUMENTS

| | | |
|---|---|---|
| 235,449 | 12/1880 | Newton . |
| 659,266 | 10/1900 | Stewart . |
| 728,828 | 5/1903 | Arkell . |
| 782,977 | 2/1905 | Madden . |
| 1,507,949 | 9/1924 | Angier . |
| 1,582,842 | 4/1926 | Lorenz . |
| 2,007,047 | 7/1935 | Gibbs ................................ 154/33 |
| 2,158,929 | 5/1939 | Dunajeff ........................... 29/180 |
| 2,177,490 | 10/1939 | Kieffer ............................. 154/33 |
| 2,257,428 | 9/1941 | Ruegenberg .................... 154/55 |
| 2,679,887 | 6/1954 | Doyle et al. ................ 154/33.05 |
| 2,896,692 | 7/1959 | Villoresi ..................... 154/33.05 |
| 2,901,951 | 9/1959 | Hochfeld .......................... 93/84 |
| 2,974,716 | 3/1961 | Fourness ........................ 154/31 |
| 3,151,947 | 10/1964 | Hastings ........................ 29/180 |
| 3,236,718 | 2/1966 | Chohn et al. .................. 161/128 |
| 3,313,080 | 4/1967 | Gewiss ........................... 52/618 |
| 3,351,441 | 11/1967 | Gewiss ........................... 29/183 |
| 3,362,118 | 1/1968 | Brunner .......................... 52/284 |
| 3,542,634 | 11/1970 | Such et al. .................... 161/88 |
| 3,550,423 | 12/1970 | Gewiss ........................... 72/363 |
| 3,726,408 | 4/1973 | Gewiss .......................... 210/493 |
| 3,817,827 | 6/1974 | Benz ............................. 162/113 |
| 3,828,784 | 8/1974 | Zoephel ......................... 128/287 |
| 3,843,761 | 10/1974 | Bierenbaum et al. .......... 264/210 R |
| 3,860,003 | 1/1975 | Buell ............................. 128/287 |
| 3,894,352 | 7/1975 | Hooker ........................... 46/1 L |
| 3,929,135 | 12/1975 | Thompson ...................... 128/287 |
| 3,969,473 | 7/1976 | Meek .............................. 264/90 |
| 3,975,455 | 8/1976 | Falender et al. ............... 260/827 |
| 3,992,162 | 11/1976 | Gewiss ......................... 29/193.5 |
| 4,082,877 | 4/1978 | Shadle .......................... 428/35 |
| 4,101,625 | 7/1978 | Haley ........................... 264/287 |
| 4,104,430 | 8/1978 | Fenton .......................... 428/175 |
| 4,110,391 | 8/1978 | Berzen et al. ................ 264/120 |
| 4,153,664 | 5/1979 | Sabee ........................... 264/289 |
| 4,321,924 | 3/1982 | Ahr ............................... 128/287 |
| 4,324,246 | 4/1982 | Mullane et al. ................. 128/287 |

(List continued on next page.)

FOREIGN PATENT DOCUMENTS

| | | |
|---|---|---|
| 0467184 | 1/1992 | European Pat. Off. . |
| 0511905 | 11/1992 | European Pat. Off. . |
| 0 307 871 B1 | 12/1992 | European Pat. Off. . |
| WO93/25171 | 12/1991 | WIPO . |

*Primary Examiner*—James J. Bell
*Attorney, Agent, or Firm*—Kevin C. Johnson; Steven W. Miller; Jacobus C. Rasser

[57] ABSTRACT

A web material which exhibits an elastic-like behavior along at least one axis when subjected to an applied and subsequently released elongation. The web material includes a strainable network having at least two visually distinct regions of the same material composition. The first region undergoes a molecular-level deformation and the second region initially undergoes a substantially geometric deformation when the web material is subjected to an applied elongation in a direction substantially parallel to the axis of elongation.

1 Claim, 38 Drawing Sheets

U.S. PATENT DOCUMENTS

| | | | |
|---|---|---|---|
| 4,342,314 | 8/1982 | Radel et al. | 128/287 |
| 4,425,130 | 1/1984 | DesMarais | 604/389 |
| 4,463,045 | 7/1984 | Ahr et al. | 428/131 |
| 4,554,121 | 11/1985 | Kramers | 264/103 |
| 4,589,876 | 5/1986 | Van Tilburg | 604/385 |
| 4,609,518 | 9/1986 | Curro et al. | 264/504 |
| 4,617,241 | 10/1986 | Mueller | 428/520 |
| 4,640,859 | 2/1987 | Hansen et al. | 428/105 |
| 4,719,261 | 1/1988 | Bunnelle et al. | 525/97 |
| 4,780,344 | 10/1988 | Hoberman | 428/12 |
| 4,834,741 | 5/1989 | Sabee | 604/385.2 |
| 4,940,462 | 7/1990 | Salerno | 604/387 |
| 4,950,264 | 8/1990 | Osborn | 604/385.1 |
| 4,968,313 | 11/1990 | Sabee | 604/385.2 |
| 5,006,394 | 4/1991 | Baird | 428/138 |
| 5,008,140 | 4/1991 | Schmertz | 428/179 |
| 5,028,474 | 7/1991 | Czaplicki | 428/178 |
| 5,034,078 | 7/1991 | Hodgson, Jr. et al. | 156/85 |
| 5,125,918 | 6/1992 | Seidy | 604/386 |
| 5,143,774 | 9/1992 | Cancio et al. | 428/169 |
| 5,151,092 | 9/1992 | Buell et al. | 604/385.2 |
| 5,196,000 | 3/1993 | Clear et al. | 604/385.2 |
| 5,202,173 | 4/1993 | Wu et al. | 528/131 |
| 5,209,801 | 5/1993 | Smith | 156/161 |
| 5,234,422 | 8/1993 | Sneller et al. | 604/385.2 |
| 5,254,111 | 10/1993 | Cancio et al. | 604/385 |
| 5,268,213 | 12/1993 | Murakami et al. | 428/163 |
| 5,296,184 | 3/1994 | Wu et al. | 264/154 |
| 5,344,691 | 9/1994 | Hanschen et al. | 428/910 |
| 5,422,178 | 6/1995 | Swenson et al. | 418/910 |
| 5,422,691 | 6/1995 | Swenson et al. | 428/910 |

WEB MATERIALS EXHIBITING ELASTIC-LIKE BEHAVIOR

This is a continuation of application Ser. No. 08/566,203, filed on Dec. 1, 1995 now abandoned which is a Division of 08/203,087 Feb. 28, 1994, issued as U.S. Pat. No. 5,518,801 which is a C-I-P of 08/100,958 Aug. 3, 1993, now abandoned.

FIELD OF THE INVENTION

The present invention relates to web materials, and more particularly, to such web materials which exhibit an elastic-like behavior in response to an applied and subsequently released (i.e., cycled) elongation along at least one axis.

The present invention has further relation to web materials wherein the inherent properties of a given web material, e.g., the resistive force exerted by the web material to an applied elongation can be modified. Additionally, staged resistive forces, lateral contraction, and/or direction of elastic-like behavior of conventional web materials can also be modified and/or provided as desired in web materials of the present invention.

Web materials of the present invention have a wide range of potential uses in both durable and disposable articles, but are particularly well suited for use in disposable absorbent articles such as sanitary napkins, bandages, pantiliners, disposable diapers, incontinent briefs, and the like.

BACKGROUND OF THE INVENTION

Absorbent articles such as sanitary napkins, pantiliners, disposable diapers, incontinent briefs, and bandages are designed to absorb and retain liquid and other discharges from the human body and to prevent body and clothing soiling. Typically, most disposable absorbent articles are made of materials that will not readily stretch under the forces that the absorbent article is normally subjected to when worn. The inability of the materials comprising the absorbent article to stretch when subjected to normal wearing forces causes the absorbent article to have certain drawbacks. One drawback is the lack of comfort for the wearer. The wearer should ideally be able to notice a difference between an absorbent article that stretches to conform to the wearer's body with the wearer's movements and an absorbent article that fails to stretch. For example, a conventional prior art sanitary napkin does not move with the wearer's undergarments, thereby causing the sanitary napkin to shift which may cause a degree of discomfort for the wearer. Enabling all or a portion of a sanitary napkin to stretch under normal wearing conditions and forces will permit the sanitary napkin to better conform to the wearer's undergarment and stay in place even when the wearer moves.

Several attempts have been made to make one or more components of absorbent articles stretchable in response to relatively low wearing forces. Typical prior art solutions rely on the addition of traditional elastics such as natural or synthetic rubber. For example, traditional elastics have been secured to portions of the topsheet and/or backsheet of absorbent articles, such as the waist portion of a disposable diaper, to provide a better fit and overall comfort for the wearer. However, traditional elastics are costly and require a certain degree of manipulation and handling during assembly. While traditional elastics do provide a degree of stretch for the absorbent article, the materials to which the traditional elastic is secured are typically not normally considered elastic or stretchable. Therefore, the added traditional elastics must be prestretched prior to being secured to the material or the material must be subjected to mechanical processing, e.g., ring rolling, to permanently elongate the material to extend beyond its initial untensioned length and allow the added traditional elastic to be effective. Otherwise, the added traditional elastic is restrained by the material and is rendered inoperable. An example of an absorbent article having a web material which has been subjected to additional processing to allow the web material to more easily extend with the added traditional elastic member is disclosed in U.S. Pat. No. 5,151,092 issued to Buell et al. on Sep. 29, 1992 and hereby incorporated herein by reference. The Buell patent describes an operation which prestrains a backsheet so that the backsheet will, upon mechanical stretching, be permanently elongated and not fully return to its original undistorted configuration. Buell teaches that a traditional elastic member must be added to the prestrained backsheet material for the invention to be operable. Buell also discloses that a prestrained backsheet improves the extension and the heat-shrink contraction of the added traditional elastic member.

Accordingly, it is an object of the present invention to provide web materials which exhibit an "elastic-like" behavior in the direction of applied elongation without the use of added traditional elastic. As used herein, the term "elastic-like" describes the behavior of web materials which when subjected to an applied elongation, the web materials extend in the direction of applied elongation and when the applied elongation is released the web materials return, to a substantial degree, to their untensioned condition. While such web materials exhibiting an elastic-like behavior have a wide range of utility, e.g. durable articles of apparel, disposable articles of apparel, covering materials such as upholstery, wrapping materials for complex shapes and the like, they are particularly well suited for use as a topsheet, a backsheet, and/or an absorbent core in an absorbent article.

SUMMARY OF THE INVENTION

The present invention pertains, in a preferred embodiment, to a web material which exhibits an elastic-like behavior in response to an applied and subsequently released elongation without the addition of traditional elastic materials such as natural or synthetic rubber.

Another elastic-like behavior that the web material of the present invention may exhibit is an initial elongation and partial recovery which results in the web material not returning to its untensioned length, i.e., the web material has undergone a degree of permanent set or deformation and has a new longer untensioned length. The web material may exhibit an elastic-like behavior in response to subsequent elongations of the web material beyond the new longer untensioned length.

Another elastic-like behavior that can be exhibited is an elongation and recovery with a definite and sudden increase in the force resisting elongation where this definite and sudden increase in resistive force restricts further elongation against relatively small elongation forces. The definite and sudden increase in the force resisting elongation is referred to as a "force wall". As used herein, the term "force wall" refers to the behavior of the resistive force of a web material during elongation wherein at some point in the elongation, distinct from the untensioned or starting point, the force resisting the applied elongation suddenly increases. After reaching the force wall, additional elongation of the web material is only accomplished via an increase in the elongation force to overcome the higher resistive force of the web material.

The web material of the present invention includes a strainable network having at least two visually distinct and dissimilar regions comprised of the same material composition. The first region is oriented substantially parallel to an axis of elongation such that it will undergo a molecular-level deformation in response to an applied axial elongation in a direction substantially parallel to the axis before a substantial portion of the second region undergoes any substantial molecular-level deformation. As used herein, the term "substantially parallel" refers to an orientation between two axes whereby the subtended angle formed by the two axes or an extension of the two axes is less than 45°. In the case of a curvilinear element it may be more convenient to use a linear axis which represents an average of the curvilinear element. The second regions initially undergo a substantially geometric deformation in response to an applied elongation in a direction substantially parallel to the axis.

In a particularly preferred embodiment, the second region is comprised of a plurality of raised rib-like elements. As used herein, the term "rib-like element" refers to an embossment, debossment or combination thereof which has a major axis and a minor axis. Preferably, the major axis is at least as long as the minor axis. The major axes of the rib-like elements are preferably oriented substantially perpendicular to the axis of applied elongation. The major axis and the minor axis of the rib-like elements may each be linear, curvilinear or a combination of linear and curvilinear. As used herein, the term "substantially perpendicular" refers to an orientation between two axes whereby the subtended angle formed by the two axes or an extension of the two axes is greater than 45°. In the case of a curvilinear element it may be more convenient to use a linear axis which represents an average of the curvilinear element.

The rib-like elements allow the second region to undergo a substantially "geometric deformation" which results in significantly less resistive forces to an applied elongation than that exhibited by the "molecular-level deformation" of the first region. As used herein, the term "molecular-level deformation" refers to deformation which occurs on a molecular level and is not discernible to the normal naked eye. That is, even though one may be able to discern the effect of molecular-level deformation, e.g., elongation of the web material, one is not able to discern the deformation which allows or causes it to happen. This is in contrast to the term "geometric deformation". As used herein the term "geometric deformation" refers to deformations of the web material which are discernible to the normal naked eye when the web material or articles embodying the web material are subjected to an applied elongation. Types of geometric deformation include, but are not limited to bending, unfolding, and rotating.

Yet another elastic-like behavior that the web material of the present invention may exhibit is an elongation and recovery with two or more significantly different force walls. This type of elastic-like behavior would be experienced if for example, after reaching a first force wall, sufficient elongation force was applied to overcome the first force wall and continue to elongate the web until a second force wall was encountered.

When the web material of the present invention has multiple or staged force walls, rib-like elements in one or more of the second regions reach their limit of geometric deformation and become essentially coplanar with the material in the first region, thereby causing the web material to exhibit a first force wall. Further elongation of the web material molecularly deforms the rib-like elements which have reached their limit of geometric deformation, and simultaneously geometrically deforms the rib-like elements in the remaining second regions until they reach their limit of geometric deformation thereby causing the web material to exhibit a second force wall.

In another preferred embodiment, the web material of the present invention exhibits at least two significantly different stages of resistive force to an applied elongation along at least one axis when subjected to an applied elongation in a direction substantially parallel to the axis. The web material includes a strainable network having at least two visually distinct regions. One of the regions is configured such that it will exhibit resistive forces in response to an applied axial elongation in a direction substantially parallel to the axis before a substantial portion of the other region develops any significant resistive force to the applied elongation. At least one of the regions has a surface-pathlength which is greater than that of the other region as measured substantially parallel to the axis while the material is in an untensioned condition. The region exhibiting the longer surface-pathlength includes one or more rib-like elements which extend beyond the plane of the other region. The web material exhibits first resistive forces to the applied elongation until the elongation of the web material is sufficient to cause a substantial portion of the region having the longer surface-pathlength to enter the plane of applied elongation, whereupon the web of material exhibits second resistive forces to further elongation. The total resistive force to elongation is higher than the first resistive force to elongation provided by the first region.

Preferably, the first region has a first surface-pathlength, L1, as measured substantially parallel to the axis of elongation while the web material is in an untensioned condition. The second region has a second surface-pathlength, L2, as measured substantially parallel to the axis of elongation while the web is in an untensioned condition. The first surface-pathlength, L1, is less than the second surface-pathlength, L2. The first region preferably has an elastic modulus, E1, and a cross-sectional area, A1. The first region produces by itself a resistive force, P1, due to molecular-level deformation in response to an applied axial elongation, D. The second region preferably has an elastic modulus, E2, and a cross-sectional area, A2. The second region produces a resistive force, P2, due to geometric deformation in response to the applied axial elongation, D. The resistive force, P1, is significantly greater than the resistive force, P2, so long as (L1+D) is less than L2.

Preferably, when (L1+D) is less than L2 the first region provides an initial resistive force, P1, in response to the applied axial elongation, D, substantially satisfying the equation P1=(A1×E1×D)/L1. When (L1+D) is greater than L2 the first and second regions provide a total resistive force, PT, to the applied axial elongation, D, satisfying the equation.

$$PT = \frac{(A1 \times E1 \times D)}{L1} + \frac{(A2 \times E2 \times |L1 + D - L2|)}{L2}$$

In another preferred embodiment, the web material exhibits a Poisson lateral contraction effect less than about 0.4 at 20% elongation as measured perpendicular to the axis of elongation. As used herein, the term "Poisson lateral contraction effect" describes the lateral contraction behavior of a material which is being subjected to an applied elongation. Preferably, the web material exhibits a Poisson lateral contraction effect less than about 0.4 at 60% elongation as measured perpendicular to the axis of elongation.

Preferably, the surface-pathlength of the second region is at least about 15% greater than that of the first region as measured parallel to the axis of elongation while the web material is in an untensioned condition. More preferably, the surface-pathlength of the second region is at least about 30% greater than that of the first region as measured parallel to the axis of elongation while the web is in an untensioned condition.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numerals identify like elements and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "absorbent article" is intended to include diapers, catamenial pads, sanitary napkins, pantiliners, incontinent briefs, bandages, and the like. The term "disposable" is used herein to describe absorbent articles which are not intended to be laundered or otherwise restored or reused as an absorbent article (i.e., they are intended to be discarded after a single use, and, preferably, to be recycled, composed or otherwise disposed of in an environmentally compatible manner). Because of their single use nature, low cost materials and methods of construction are highly desirable in disposable absorbent articles.

Figure 1:
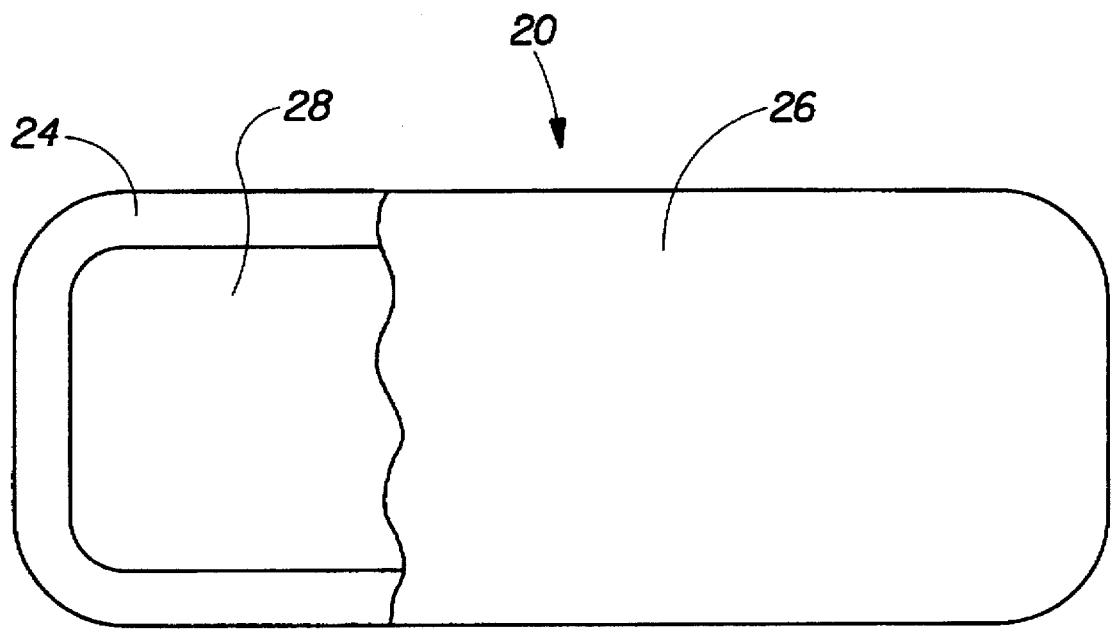
FIG. 1 is a simplified plan view illustration of a prior art sanitary napkin with portions cut-away to more clearly show the construction of the sanitary napkin.

FIG. 1 is a plan view of a prior art sanitary napkin 20 with portions of the structure being cut-away to more clearly show the construction of the sanitary napkin 20 and with the portion of the sanitary napkin 20 which faces away from the wearer, i.e., the outer surface, oriented towards the viewer. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). As shown in FIG. 1, the sanitary napkin 20 comprises a liquid pervious topsheet 24, a liquid impervious backsheet 26 joined with the topsheet 24, and an absorbent core 28 positioned between the topsheet 24 and the backsheet 26.

While the topsheet, backsheet, and absorbent core may be assembled in a variety of well known configurations (including so called "tube" products or side flap products), preferred sanitary napkin configurations are described generally in U.S. Pat. No. 4,950,264, issued to Osborn on Aug. 21, 1990; U.S. Pat. No. 4,425,130, issued to DesMarais on Jan. 10, 1984; U.S. Pat. No. 4,321,924, issued to Ahr on Mar. 30, 1982; and U.S. Pat. No. 4,589,876, issued to Van Tilburg on Aug. 18, 1987. Each of these patents are hereby incorporated herein by reference.

Figure 2:
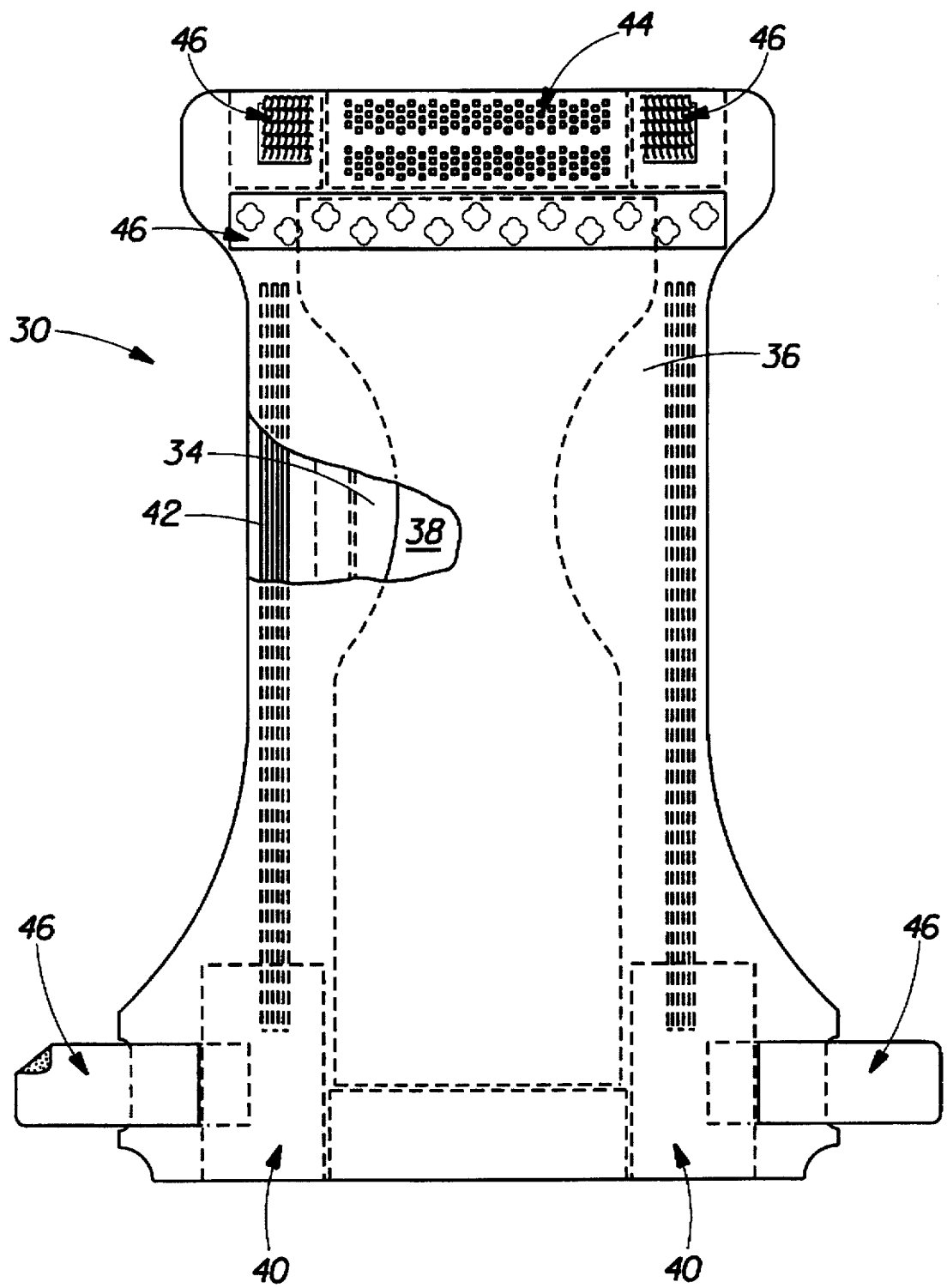
FIG. 2 is a simplified plan view illustration of a prior art disposable diaper with portions cut-away to more clearly show the construction of the disposable diaper.

FIG. 2 is a plan view of a prior art disposable diaper 30 in its uncontracted state (i.e., with elastic induced contraction pulled out except in the side panel wherein the elastic is left in its relaxed condition) with portions of the structure being cut-away to more clearly show the construction of the diaper 30 and with the portion of the diaper 30 which faces away from the wearer, i.e., the outer surface, oriented towards the viewer. As used herein, the term "diaper" refers to an absorbent article generally worn by infants and incontinent persons that is worn about the lower torso of the wearer. As shown in FIG. 2, the diaper 30 comprises a liquid pervious topsheet 34, a liquid impervious backsheet 36 joined with the topsheet 34, an absorbent core 38 positioned between the topsheet 34 and the backsheet 36, elasticized side panels 40, elasticized leg cuffs 42, an elastic waist feature 44, and a fastening system generally multiply designated as 46.

While the diaper 30 may be assembled in a variety of well known configurations, preferred diaper configurations are described generally in U.S. Pat. No. 3,860,003, issued to Kenneth B. Buell on Jan. 14, 1975; and U.S. Pat. No. 5,151,092 issued to Kenneth B. Buell et al. on Sep. 29, 1992. Each of these patents are hereby incorporated herein by reference.

While the present invention will be described in the content of providing a "web material" which exhibits elastic-like behavior to an applied and subsequently released elongation which is particularly well suited for use as a backsheet, a topsheet and/or an absorbent core or a portion thereof on a disposable absorbent article such as a disposable diaper, sanitary napkin, or bandage the present invention is in no way limited to such application. It may be employed in nearly any application where a relatively low cost elastic-like web material is desired, e.g., durable articles of apparel, such as exercise clothing, disposable articles of apparel, elastic bandages, upholstery or wrapping material used to cover complex shaped articles, etc. As used herein the term "web material" refers to a sheet-like material, e.g., a topsheet, backsheet, or absorbent core on a disposable absorbent article, a composite or laminate of two or more sheet-like materials and the like. The present invention may be practiced to great advantage in many situations where it is desirable to produce a web material which exhibits an elastic-like behavior to an applied and subsequently released elongation along at least one axis. The detailed description of a preferred structure and its use as a backsheet on a sanitary napkin or a disposable diaper will allow one skilled in the art to readily adapt the present invention to other applications.

Figure 3:
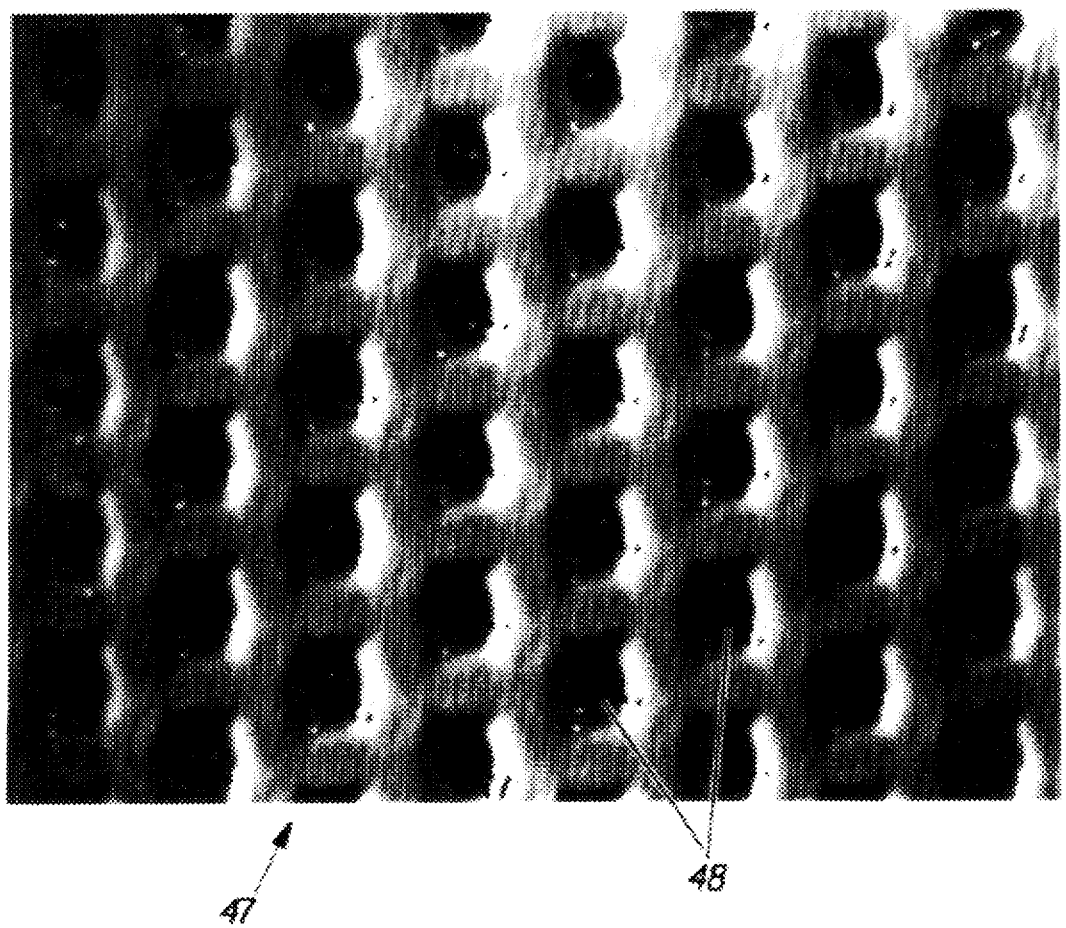
FIG. 3 is a plan view photograph of a prior art deeply embossed polymeric web with the embossments facing away from the viewer.
Figure 4:
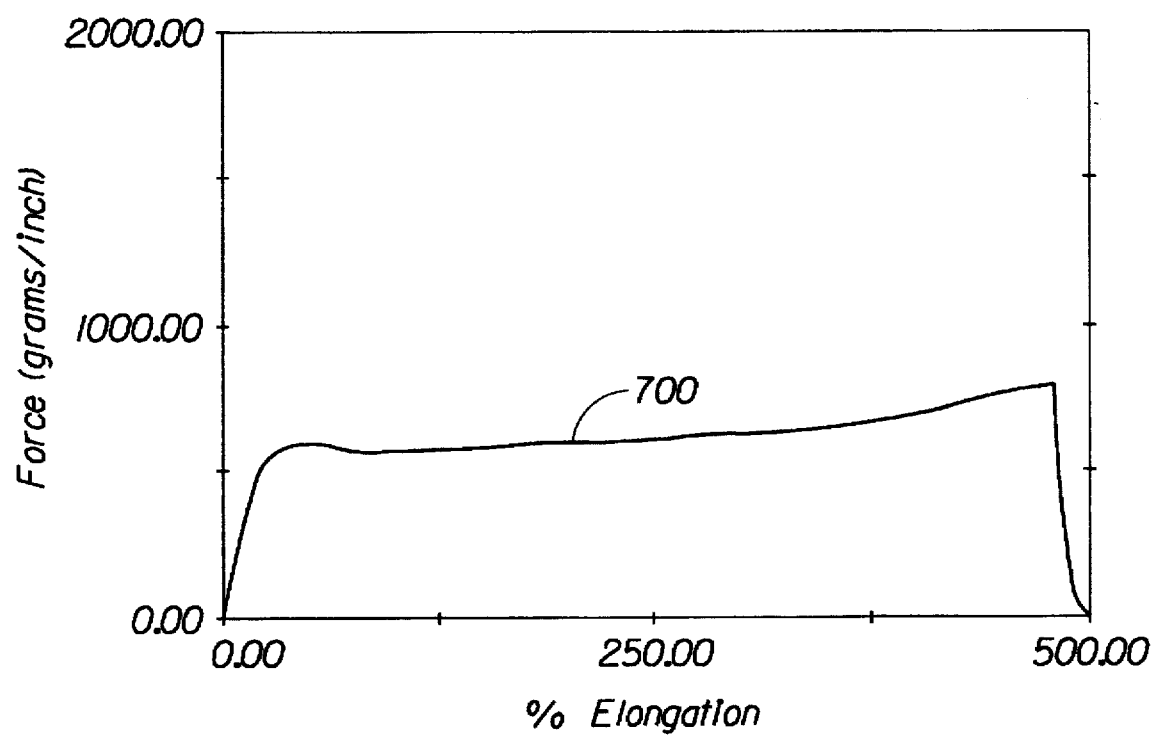
FIG. 4 is a graph of the resistive force versus percent elongation of the prior art deeply embossed web of FIG. 3.

FIG. 3 is a plan view photograph of a prior art deeply embossed polymeric web 47 which has been used as a backsheet on prior art absorbent articles. Specifically, the deeply embossed web 47 is available from Tredegar Film Products, Terra Haute, Ind. under the designation ULAB X-5430. The deeply embossed web 47 comprises a pattern of embossments 48. FIG. 4 is a resistive force-elongation curve 700 of the deeply embossed polymeric web 47 of FIG. 3. The method of generating the resistive force-elongation curve 700 can be found in the Test Methods section set forth in subsequent portions of the present specification. As can be seen in FIG. 4, the deeply embossed web 47 has a resistive force-elongation curve 700 which is substantially the same shape as the resistive force-elongation curve 710, shown in FIG. 6, of a typical unembossed web of similar composition; that is, the resistive force-elongation curve 700 follows a substantially single stage, continuous curve in which the force increases steeply and at a substantially uniform rate until beginning to yield. Thus, it is clear that this pattern of embossments 48 in web 47 do not significantly alter the resistive force-elongation properties of the deeply embossed web 47 as compared to an unembossed base web of similar material composition.

Despite widespread use of the prior art deeply embossed polymeric web 47 as a backsheet on disposable absorbent articles, the deeply embossed polymeric web does not offer any functionally enhanced properties when compared to an unembossed base web, i.e., improved conformance, stretch behavior and/or garment-like fit. This is believed due to the fact that the resistive force versus elongation characteristics of the deeply embossed web are not significantly different than those of an otherwise identical planar, base web, i.e., both webs exhibit a substantially single stage higher resistive force versus elongation curve of the type generally shown in FIG. 4.

Figure 5:
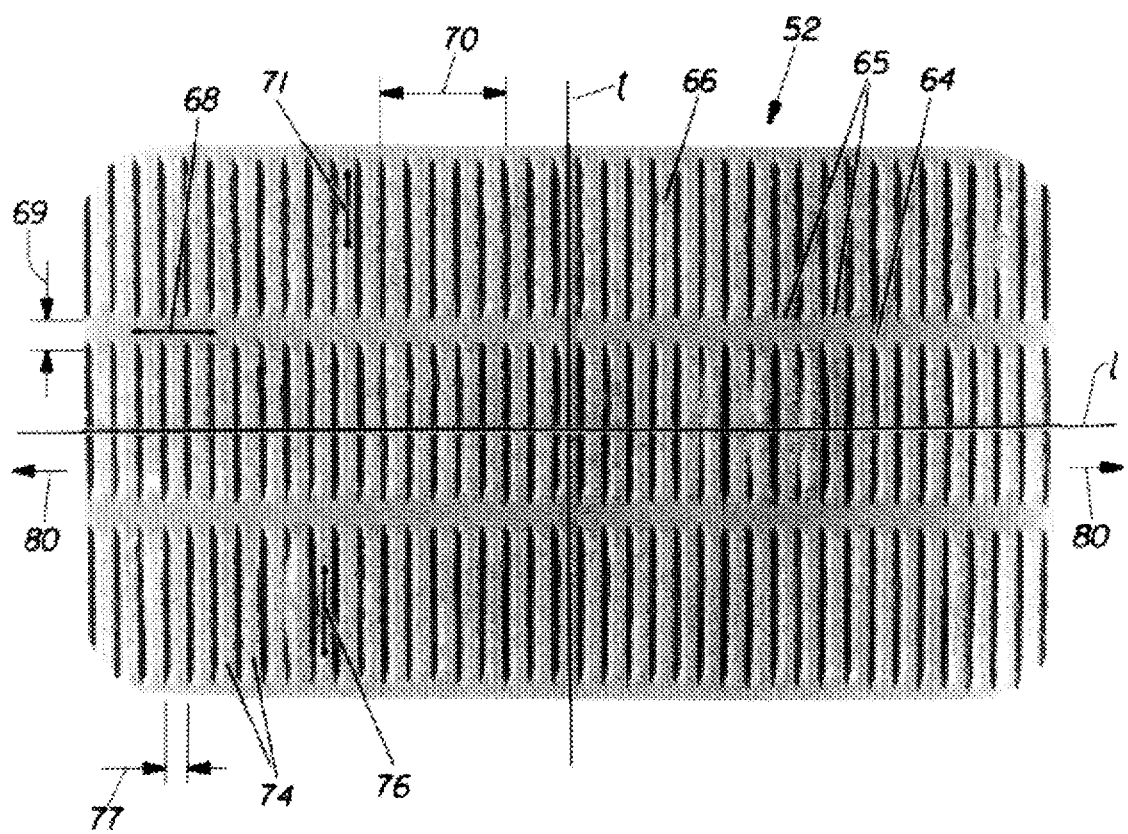
FIG. 5 is a plan view photograph of a preferred embodiment of a polymeric web material having a first region and a second region of the present invention with the rib-like elements of the second region facing toward the viewer.

Referring now to FIG. 5, there is shown a preferred embodiment of a polymeric web material 52 of the present invention. The web material 52 is shown in FIG. 5 in its substantially untensioned condition. The web material 52 is particularly well suited for use as a backsheet on an absorbent article, such as the sanitary napkin 20 in FIG. 1 or the disposable diaper 30 in FIG. 2. The web material 52 has two centerlines, a longitudinal centerline, which is also referred to hereinafter as an axis, line, or direction "l" and a transverse of lateral centerline, which is also referred to hereinafter as an axis, line, or direction "t". The transverse centerline "t" is generally perpendicular to the longitudinal centerline "l".

Figure 5A:
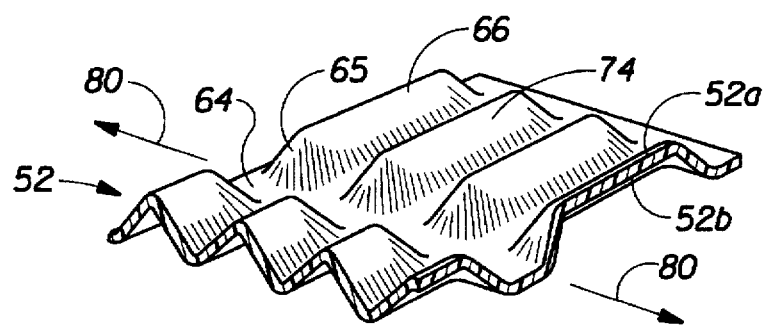
FIG. 5A is a segmented, perspective illustration of the polymeric web material of FIG. 5 in an untensioned condition.

Referring now to FIGS. 5 and 5A, web material 52 includes a "strainable network" of distinct regions. As used herein, the term "strainable network" refers to an interconnected and interrelated group of regions which are able to be extended to some useful degree in a predetermined direction providing the web material with an elastic-like behavior in response to an applied and subsequently released elongation. The strainable network includes at least a first region 64 and a second region 66. Web material 52 includes a transitional region 65 which is at the interface between the first region 64 and the second region 66. The transitional region 65 will exhibit complex combinations of the behavior of both the first region and the second region. It is recognized that every embodiment of the present invention will have a transitional region, however, the present invention is defined by the behavior of the web material in the first region 64 and the second region 66. Therefore, the ensuing description of the present invention will be concerned with the behavior of the web material in the first regions and the second regions only since it is not dependent upon the complex behavior of the web material in the transitional regions 65.

Web material 52 has a first surface 52a and an opposing second surface 52b. In the preferred embodiment shown in FIGS. 5 and 5A, the strainable network includes a plurality of first regions 64 and a plurality of second regions 66. The first regions 64 have a first axis 68 and a second axis 69, wherein the first axis 68 is preferably longer than the second axis 69. The first axis 68 of the first region 64 is substantially parallel to the longitudinal axis of the web material 52 while the second axis 69 is substantially parallel to the transverse axis of the web material 52. Preferably, the second axis of the first region, the width of the first region, is from about 0.01 inches to about 0.5 inches, and more preferably from about 0.03 inches to about 0.25 inches. The second regions 66 have a first axis 70 and a second axis 71. The first axis 70 is substantially parallel to the longitudinal axis of the web material 52, while the second axis 71 is substantially parallel to the transverse axis of the web material 52. Preferably, the second axis of the second region, the width of the second region, is from about 0.01 inches to about 2.0 inches, and more preferably from about 0.125 inches to about 1.0 inches. In the preferred embodiment of FIG. 5, the first regions 64 and the second regions 66 are substantially linear, extending continuously in a direction substantially parallel to the longitudinal axis of the web material 52.

The first region 64 has an elastic modulus E1 and a cross-sectional area A1. The second region 66 has a modulus E2 and a cross-sectional area A2.

In the illustrated embodiment, the web material 52 has been "formed" such that the web material 52 exhibits a resistive force along an axis, which in the case of the illustrated embodiment is substantially parallel to the longitudinal axis of the web, when subjected to an applied axial elongation in a direction substantially parallel to the longitudinal axis. As used herein, the term "formed" refers to the creation of a desired structure or geometry upon a web material that will substantially retain the desired structure or geometry when it is not subjected to any externally applied elongations or forces. A web material of the present invention is comprised of at least a first region and a second region, wherein the first region is visually distinct from the second region. As used herein, the term "visually distinct" refers to features of the web material which are readily discernible to the normal naked eye when the web material or objects embodying the web material are subjected to normal use. As used herein the term "surface-pathlength" refers to a measurement along the topographic surface of the region in question in a direction substantially parallel to an axis. The method for determining the surface-pathlength of the respective regions can be found in the Test Methods section set forth in subsequent portions of the present specification.

Methods for forming web materials of the present invention include, but are not limited to embossing by mating plates or rolls, thermoforming, high pressure hydraulic forming, or casting. While the entire portion of the web 52 has been subjected to a forming operation, the present invention may also be practiced by subjecting to formation only a portion thereof, e.g., a portion of a diaper backsheet, as will be described in detail below.

In the preferred embodiment shown in FIGS. 5 and 5A, the first regions 64 are substantially planar. That is, the material within the first region 64 is in substantially the same condition before and after the formation step undergone by web 52. The second regions 66 include a plurality of raised rib-like elements 74. The rib-like elements may be embossed, debossed or a combination thereof. The rib-like elements 74 have a first or major axis 76 which is substantially parallel to the transverse axis of the web 52 and a second or minor axis 77 which is substantially parallel to the longitudinal axis of the web 52. The first axis 76 of the rib-like elements 74 is at least equal to, and preferably longer than the second axis 77. Preferably, the ratio of the first axis 76 to the second axis 77 is at least about 1:1 or greater, and more preferably at least about 2:1 or greater.

The rib-like elements 74 in the second region 66 may be separated from one another by unformed areas. Preferably, the rib-like elements 74 are adjacent one another and are separated by an unformed area of less than 0.10 inches as measured perpendicular to the major axis 76 of the rib-like elements 74, and more preferably, the rib-like elements 74 are contiguous having no unformed areas between them.

The first region 64 and the second region 66 each have a "projected pathlength". As used herein the term "projected pathlength" refers to the length of a shadow of a region that would be thrown by parallel light. The projected pathlength of the first region 64 and the projected pathlength of the second region 66 are equal to one another.

The first region 64 has a surface-pathlength, L1, less than the surface-pathlength, L2, of the second region 66 as measured topographically in a direction parallel to the longitudinal axis of the web 52 while the web is in an untensioned condition. Preferably, the surface-pathlength of the second region 66 is at least about 15% greater than that of the first region 64, more preferably at least about 30% greater than that of the first region, and most preferably at least about 70% greater than that of the first region. In general, the greater the surface-pathlength of the second region, the greater will be the elongation of the web before encountering the force wall.

Web material 52 exhibits a modified "Poisson lateral contraction effect" substantially less than that of an otherwise identical base web of similar material composition. The method for determining the Poisson lateral contraction effect of a material can be found in the Test Methods section set forth in subsequent portions of the present specification. Preferably, the Poisson lateral contraction effect of webs of the present invention is less than about 0.4 when the web is subjected to about 20% elongation. Preferably, the webs exhibit a Poisson lateral contraction effect less than about 0.4 when the web is subjected to about 40, 50 or even 60% elongation. More preferably, the Poisson lateral contraction effect is less than about 0.3 when the web is subjected to 20, 40, 50 or 60% elongation. The Poisson lateral contraction effect of webs of the present invention is determined by the amount of the web material which is occupied by the first and second regions, respectively. As the area of the web material occupied by the first region increases the Poisson lateral contraction effect also increases. Conversely, as the area of the web material occupied by the second region increases the Poisson lateral contraction effect decreases. Preferably, the percent area of the web material occupied by the first area is from about 2% to about 90%, and more preferably from about 5% to about 50%.

Web materials of the prior art which have at least one layer of an elastomeric material will generally have a large Poisson lateral contraction effect, i.e., they will "neck down" as they elongate in response to an applied force. Web materials of the present invention can be designed to moderate if not substantially eliminate the Poisson lateral contraction effect.

For web material 52, the direction of applied axial elongation, D, indicated by arrows 80 in FIG. 5, is substantially perpendicular to the first axis 76 of the rib-like elements 74. The rib-like elements 74 are able to unbend or geometrically deform in a direction substantially perpendicular to their first axis 76 to allow extension in web 52.

Figure 6:
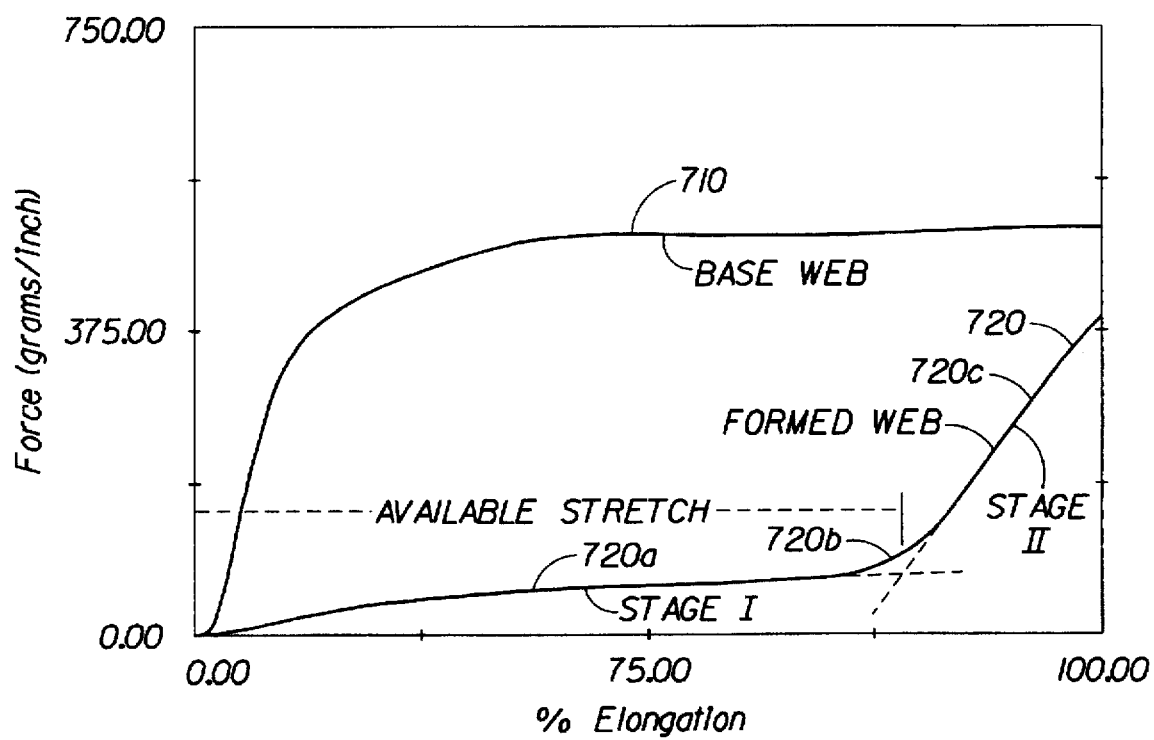
FIG. 6 is a graph of the resistive force versus percent elongation comparing the behavior of a web material of the present invention, as shown in FIG. 5, formed from Clopay 1401, with a base web of similar material composition.

In FIG. 6 there is shown a graph of the resistive force-elongation curve 720 of a web material generally similar to web material 52 shown in FIG. 5 along with a curve 710 of a base film material of similar composition. Specifically the samples are polymeric web materials, comprised substantially of linear low density polyethylene, approximately 0.001" thick, designated sample 1401 available from Clopay, Cincinnati Ohio. The method for generating the resistive force-elongation curves can be found in the Test Methods section set forth in subsequent portions of the present specification. Referring now to the force-elongation curve 720 of the formed web, there is an initial substantially linear, lower force versus elongation stage I designated 720a, a transition zone designated 720b which indicates the encounter of the force wall, and a substantially linear stage II designated 720c which displays substantially higher force versus elongation behavior.

As seen in FIG. 6 the formed web exhibits different elongation behavior in the two stages when subjected to an applied elongation in a direction parallel to the longitudinal axis of the web. The resistive force exerted by the formed web to the applied elongation is significantly less in the stage I region (720a) versus the stage II region (720c) of curve 720. Furthermore, the resistive force exerted by the formed web to the applied elongation as depicted in stage I (720a) of curve 720 is significantly less than the resistive force exerted by the base web as depicted in curve 710 within the limits of elongation stage I. As the formed web is subjected to further applied elongation and enters stage II (720c) the resistive force exerted by the formed web increases and approaches the resistive force exerted by the base web. The resistive force to the applied elongation for the stage I region (720a) of the formed web is provided by the molecular-level deformation of the first region of the formed web and the geometric deformation of the second region of the formed web. This is in contrast to the resistive force to an applied elongation that is provided by the base web, depicted in curve 710 of FIG. 6, which results from molecular-level deformation of the entire web. Web materials of the present invention can be designed to yield virtually any resistive force in stage I which is less than that of the base web material by adjusting the percentage of the web surface which is comprised of the first and second regions, respectively. The force-elongation behavior of stage I can be controlled by adjusting the width, cross-sectional area, and spacing of the first region and the composition of the base web.

Figure 5B:
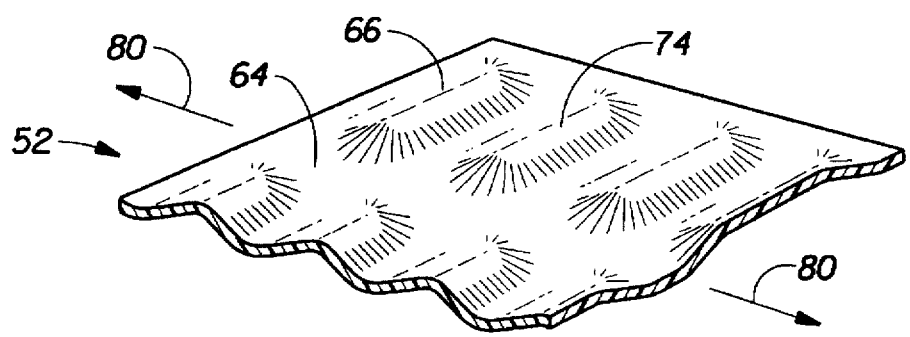
FIG. 5B is a segmented, perspective illustration of a polymeric web material of FIG. 5 in a tensioned condition corresponding to stage I on the force-elongation curve depicted in FIG. 6.
Figure 5C:
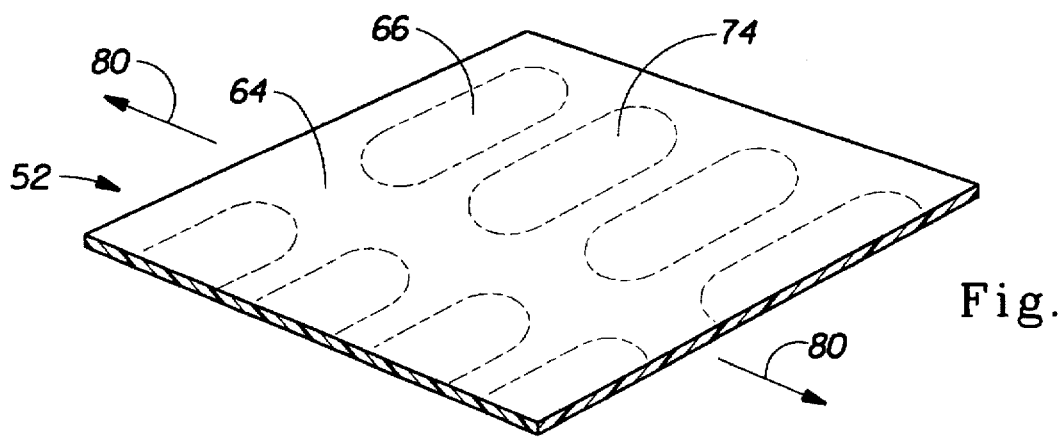
FIG. 5C is a segmented perspective illustration of the polymeric web material of FIG. 5 in a tensioned condition corresponding to stage II on the force-elongation curve depicted in FIG. 6.

Referring now to FIG. 5B, as web 52 is subjected to an applied axial elongation, D, indicated by arrows 80 in FIG. 5, the first region 64 having the shorter surface-pathlength, L1, provides most of the initial resistive force, P1, as a result of molecular-level deformation, to the applied elongation which corresponds to stage I. While in stage I, the rib-like elements 74 in the second region 66 are experiencing geometric deformation, or unbending and offer minimal resistance to the applied elongation. In the transition zone (720b) between stages I and II, the rib-like elements 74 are becoming aligned with the applied elongation. That is, the second region is exhibiting a change from geometric deformation to molecular-level deformation. This is the onset of the force wall. In stage II, as seen in FIG. 5C, the rib-like elements 74 in the second region 66 have become substantially aligned with the plane of applied elongation (i.e. the second region has reached its limit of geometric deformation) and begin to resist further elongation via molecular-level deformation. The second region 66 now contributes, as a result of molecular-level deformation, a second resistive force, P2, to further applied elongation. The resistive forces to elongation depicted in stage II by both the molecular-level deformation of the first region 64 and the molecular-level deformation of the second region 66 provide a total resistive force, PT, which is greater than the resistive force depicted in stage I which is provided by the molecular-level deformation of the first region 64 and the geometric deformation of the second region 66. Accordingly, the slope of the force-elongation curve in stage II is significantly greater than the slope of the force-elongation curve in stage I.

The resistive force P1 is substantially greater than the resistive force P2 when (L1+D) is less than L2. When (L1+D) is less than L2 the first region provides the initial resistive force P1, generally satisfying the equation:

$$P1 = \frac{(A1 \times E1 \times D)}{L1}$$

When (L1+D) is greater than L2 the first and second regions provide a combined total resistive force PT to the applied elongation, D, generally satisfying the equation:

$$PT = \frac{(A1 \times E1 \times D)}{L1} + \frac{(A2 \times E2 \times |L1 + D - L2|)}{L2}$$

The maximum elongation occurring while in stage I is the "available stretch" of the formed web material. The available stretch corresponds to the distance over which the second region experiences geometric deformation. The available stretch can be effectively determined by inspection of the force-elongation curve 720 as shown in FIG. 6. The approximate point at which there is an inflection in the transition zone between stage I and stage II is the percent elongation point of "available stretch". The range of available stretch can be varied from about 10% to 100% or more; this range of elongation is often found to be of interest in disposable absorbent articles, and can be largely controlled by the extent to which the surface-pathlength L2 in the second region exceeds the surface-pathlength L1 in the first region and the composition of the base film. The term available stretch is not intended to imply a limit to the elongation which the web of the present invention may be subjected to as there are applications where elongation beyond the available stretch is desirable.

Figure 7:
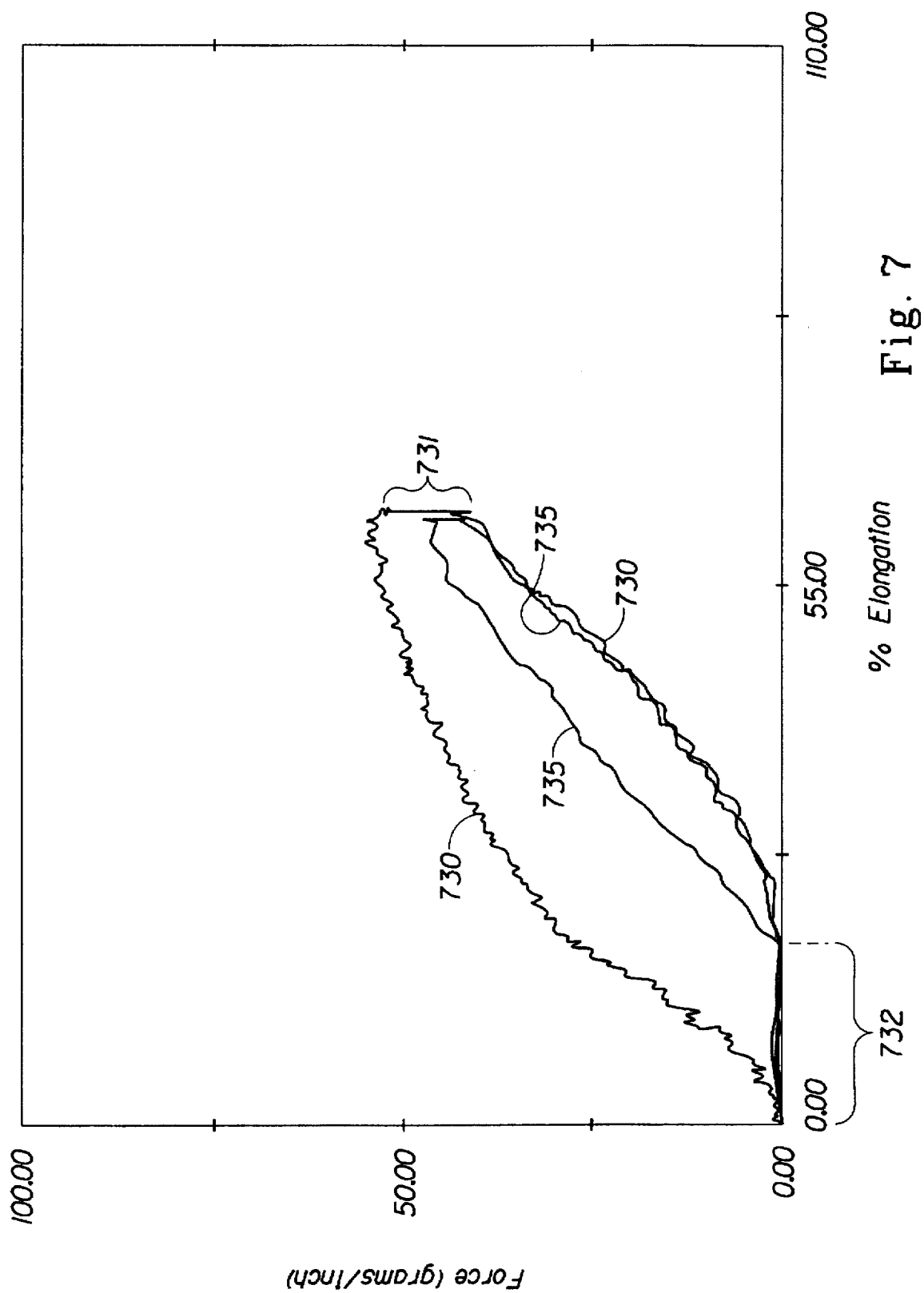
FIG. 7 is a graph of the elastic hysteresis behavior of the web material of the present invention which is graphically represented by curve 720 in FIG. 6 when the web material is subjected to a hysteresis test at 60% elongation.

The curves 730 and 735 in FIG. 7 show the elastic hysteresis behavior exhibited by a web material of the present invention which is generally similar to that used to generate curve 720 in FIG. 6. The formed web was examined for elastic hysteresis behavior at an elongation of 60%. Curve 730 represents the response to an applied and released elongation during the first cycle and curve 735 represent the response to an applied and released elongation during the second cycle. The force relaxation during the first cycle 731 and the percent set or deformation 732 are depicted in FIG. 7. Note that significant recoverable elongation, or useful elasticity, is exhibited at relatively low forces over multiple cycles, i.e., the web material can easily expand and contract to a considerable degree. The method of generating the elastic hysteresis behavior can be found in the Test Method section set forth in subsequent portion of the present specification.

Figure 8:
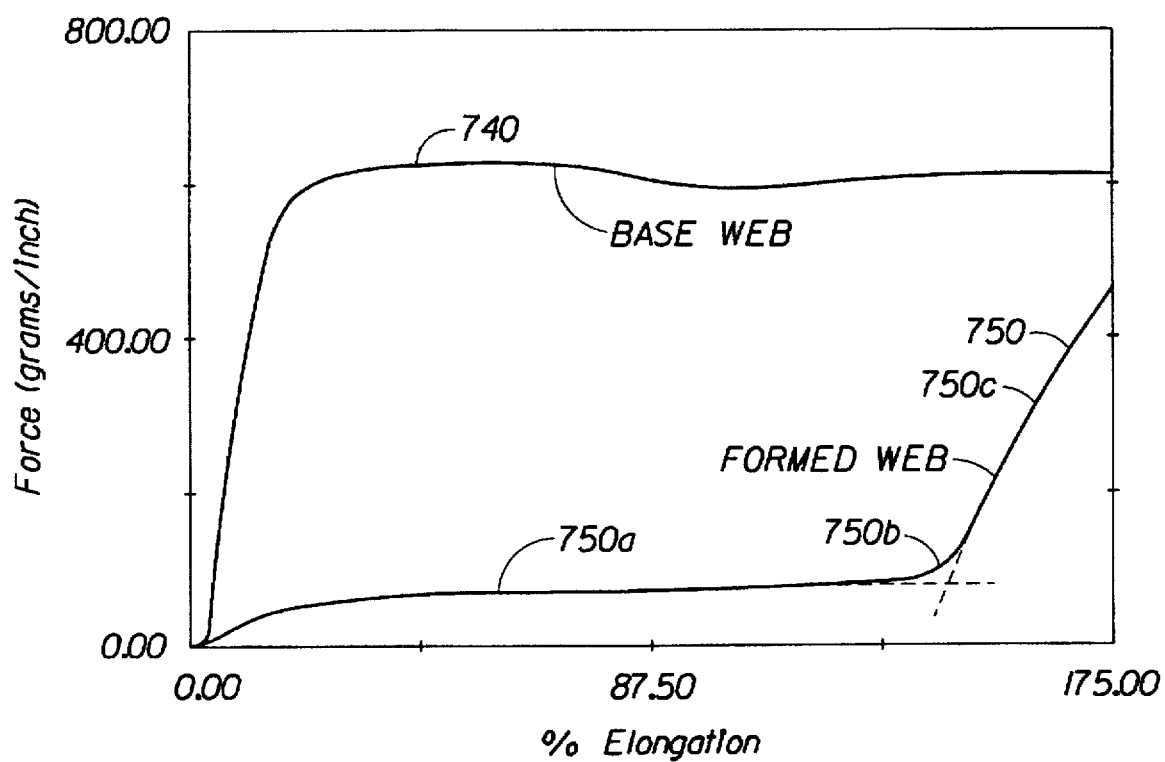
FIG. 8 is a graph of the resistive force versus percent elongation comparing the behavior of a web material of the present invention formed from Tredegar sample P-8863/X8323, with a base web of similar material composition.
Figure 9:
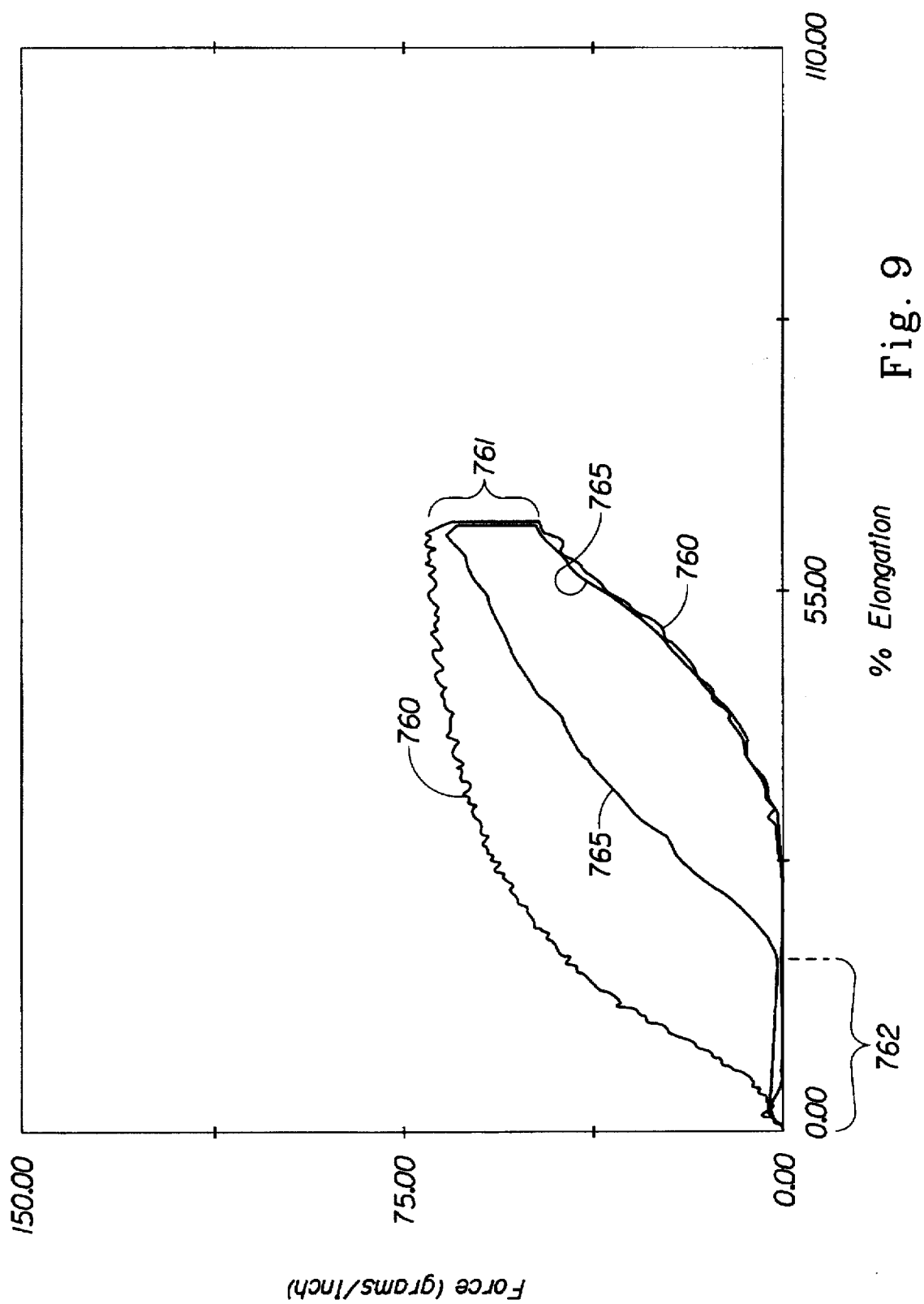
FIG. 9 is a graph of the elastic hysteresis behavior of the web material of the present invention which is graphically represented by curve 750 in FIG. 8 when the web material is subjected to a hysteresis test at 60% elongation.

FIG. 8 shows the force-elongation behavior for both a base web depicted in curve 740 and a formed web of the present invention depicted in curve 750 where both webs are comprised of a linear low density polyethylene film, approximately 0.001" thick, available from Tredegar Inc, Terre Haute, Ind., and designated P-8863/X8323. This type of base film has been successfully commercially utilized as a fluid impervious backsheet on disposable diapers. Referring now to curve 750, there is an initial substantially linear, lower force-elongation stage I designated 750a, a transition zone designated 750b, and a substantially linear stage II designated 750c. Note the distinctive lower force two-stage behavior in the formed web provided first in stage I by the combination of molecular-level deformation of the first region and geometric deformation of the second region, and then in stage II by molecular-level deformation of both the first region and the second region as depicted by curve 750 compared to the molecular-level deformation of the base web as depicted by curve 740. The curves 760 and 765 in FIG. 9 show the elastic hysteresis behavior of a formed web similar to that used to generate curve 750 in FIG. 8 when examined in 60% elongation. Curve 760 represents the response to an applied and released elongation during the first cycle and curve 765 represents the response to an applied and released elongation during the second cycle. The force relaxation during the first cycle 761 and the percent set or deformation 762 are depicted in FIG. 9. Note that there is very significant elastic recovery exhibited by the sample over this observed range of elongations over multiple cycles.

Figure 10:
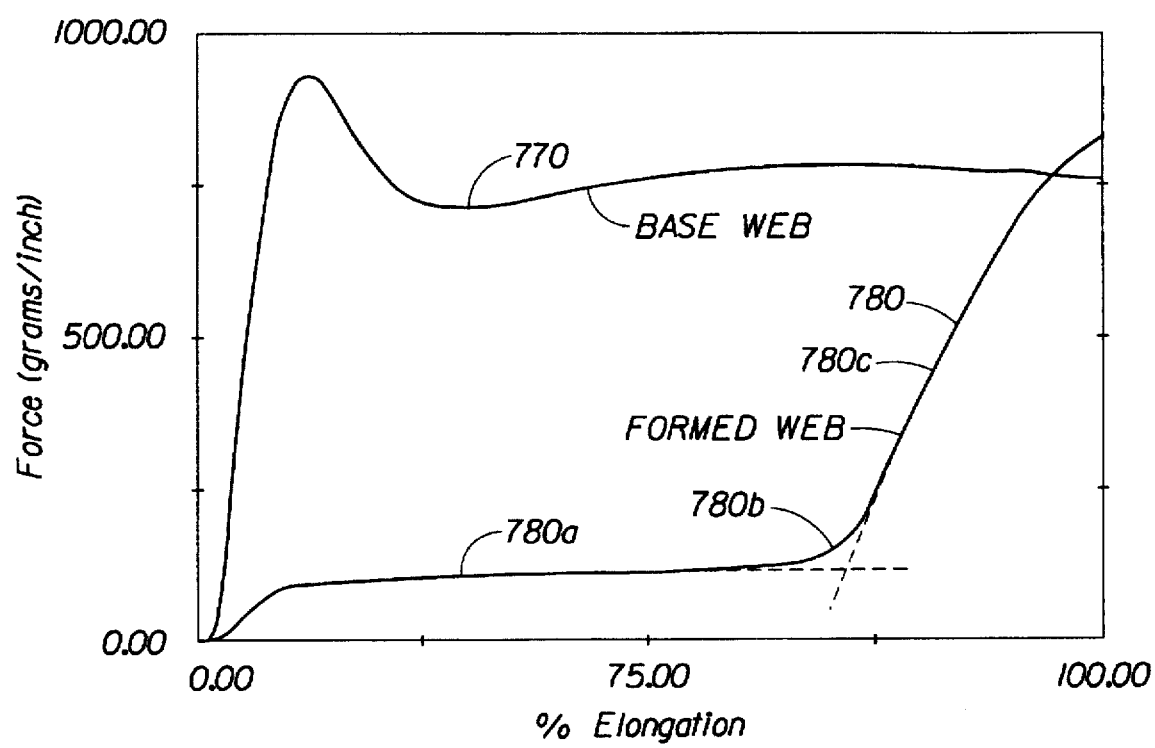
FIG. 10 is a graph of the resistive force versus percent elongation comparing the behavior of another web material of the present invention formed from, Tredegar sample X-8998, with a base web of similar material composition.
Figure 11:
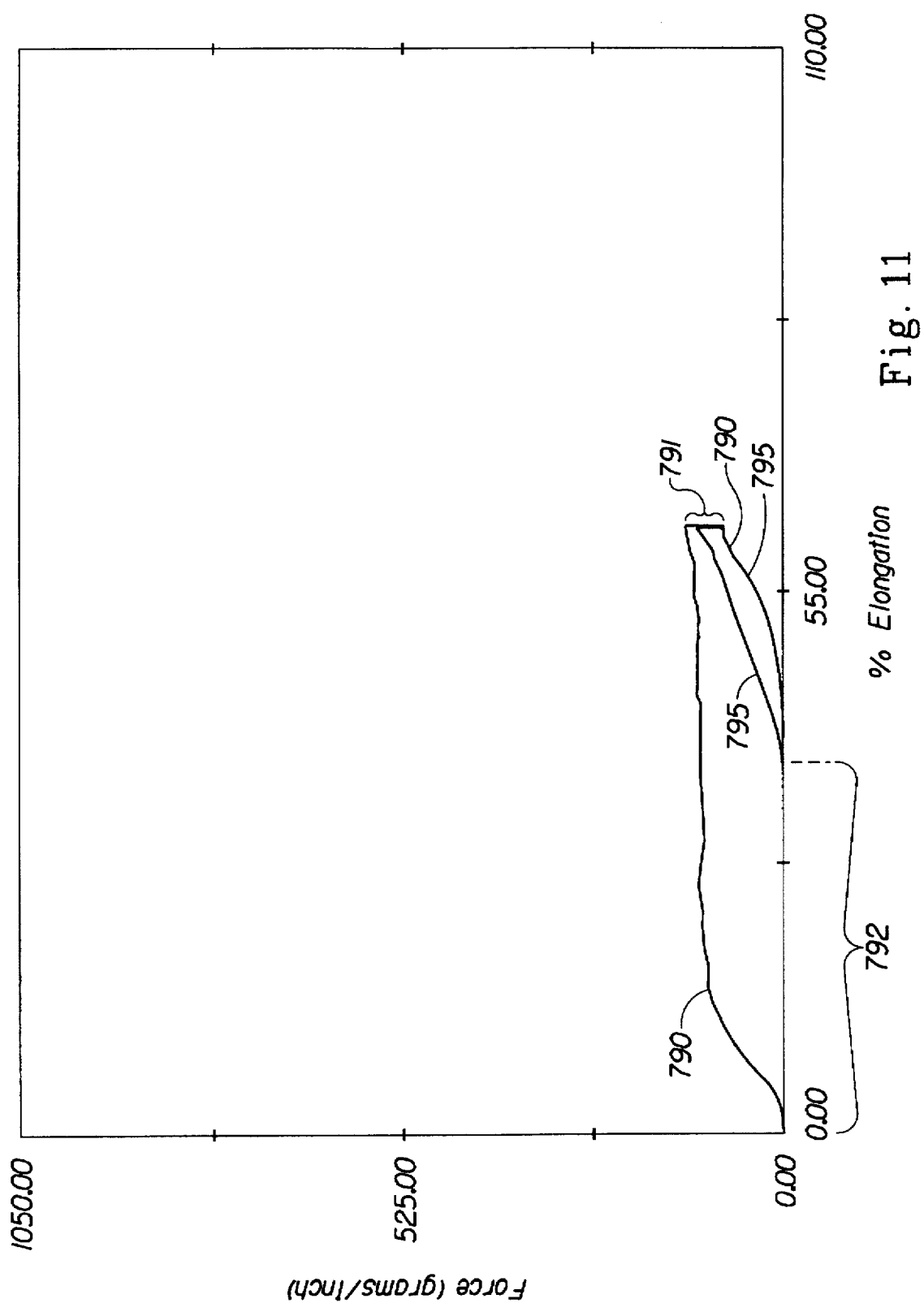
FIG. 11 is a graph of the elastic hysteresis behavior of the web material of the present invention which is graphically represented by curve 780 in FIG. 10 when the web material is subjected to a hysteresis test at 60% elongation.

FIG. 10 shows the force-elongation behavior for both a base web depicted in curve 770 and a formed web of the present invention depicted in curve 780 where both webs are comprised of a think polymeric film, approximately 0.001" thick, consisting mostly of linear medium density polyethylene plus linear low density polyethylene, available from Tredegar Inc, Terra Haute, Ind., and designated X-8998. Referring now to curve 780, there is an initial substantially linear, lower force-elongation stage I designated 780a, a transition zone designated 780b, and a substantially linear higher force-elongation stage II designated 780c. Note the distinctive lower force two-stage behavior in the formed web provided first in stage I by the combination of molecular-level deformation of the first region and geometric deformation of the second region and then in stage II molecular-level deformation of both the first region and the second region as depicted in curve 780 compared to the molecular-level deformation of the base web as depicted in curve 770. Curves 790 and 795 in FIG. 11 show the elastic hysteresis behavior of a formed web material similar to that used to generate curve 780 in FIG. 10 examined at 60% elongation. Curve 790 represents the response to an applied and released elongation during the first cycle and curve 795 represents the response to an applied and released elongation during the second cycle. The force relaxation of the web during the first cycle is depicted by 791 and the degree of set or deformation of the web material after the first cycle is depicted by 792. In this example, the web material was elongated to a point where the material in the first region which was experiencing molecular-level deformation was permanently deformed (i.e., experienced a permanent set) by the elongation. It should further be noted that the 60% elongation that produced the permanent deformation of the web material in the first region was insufficient to encounter the limits of the geometric deformation of the second region, i.e., the force wall. That is, the limits of the geometric deformation of the second region was greater than the elastic limits of the molecular-level deformation of the first region. However, this permanent deformation of the first region did not eliminate useful elastic-like behavior of the web material, but rather resulted effectively in merely a "shifting" of the untensioned point of elastic-like behavior of the web material. This is illustrated by curve 795 which depicts the behavior of the web material on the second cycle, after permanent deformation. A useful amount of elastic-like behavior will remain, even at higher levels of permanent deformation of the type illustrated by the example in FIG. 11. It is recognized that this useful elastic-like behavior will diminish at extremely high levels of elongation of the web material and subsequent high permanent deformation of the material in the first regions of the web.

Figure 12:
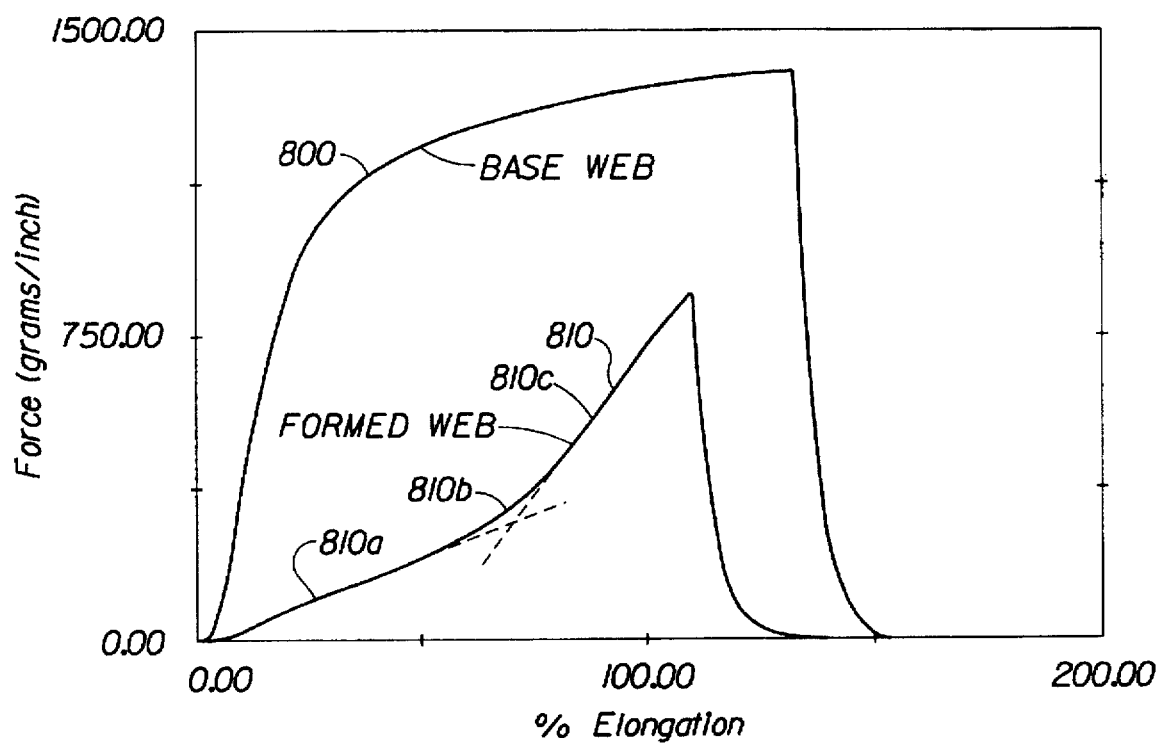
FIG. 12 is a graph of the resistive force versus percent elongation comparing the behavior of another web material of the present invention formed from, Volara 2A foam sheet, with a base web of similar material composition.
Figure 13:
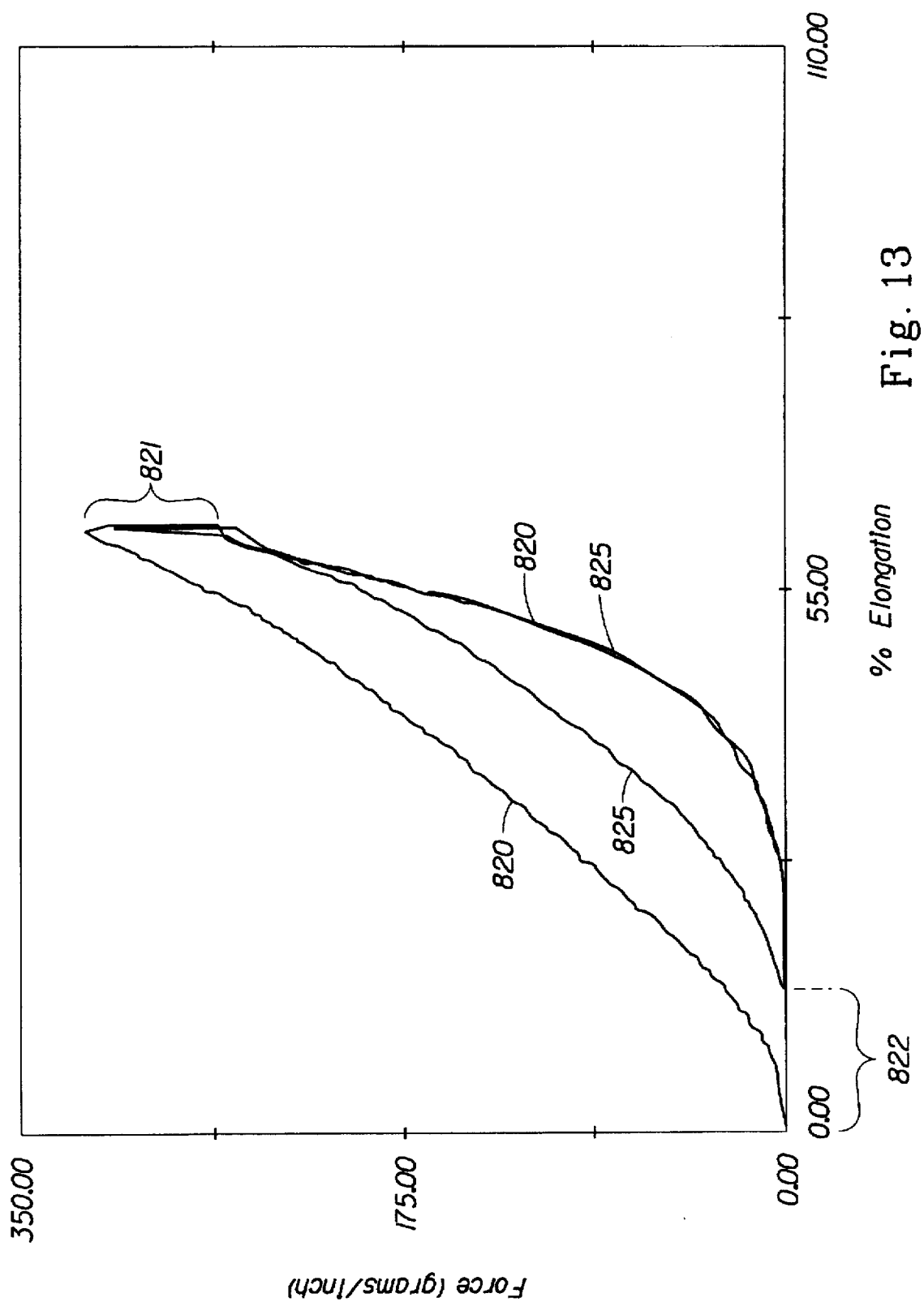
FIG. 13 is a graph of the elastic hysteresis behavior of the web material of the present invention which is graphically represented by curve 810 in FIG. 12 when the web material is subjected to a hysteresis test at 60% elongation.

FIG. 12 shows the force-elongation behavior for both a base web depicted in curve 800 and a formed web of the present invention depicted in curve 810 where both webs are comprised of a foam polyethylene sheet, approximately 0.080" thick, available as Volara 2a from Voltek Corp., Lawrence, Mass. Referring now to curve 810, there is an initial substantially linear, lower force-elongation stage I designated 810a, a transition zone designated 810b, and a substantially linear stage II designated 810c. Note the distinctive lower force two-stage behavior in the formed web provided first in stage I (810a) by the combination of molecular-level deformation of the first region and geometric deformation of the second region and then in stage II (810c) by molecular-level deformation of both the first region and the second region as depicted in curve 810 compared to the molecular-level deformation of the base web as depicted in curve 800. Note that the base foam sample undergoes failure at an elongation less than about 150% and the formed web undergoes failure at less than about 120% elongation. The curves 820 and 825 in FIG. 13 show the elastic hysteresis behavior of a formed web material similar to that used to generate curve 810 in FIG. 12 examined at 60% elongation. Curve 820 represents the response to an applied and released elongation during the first cycle and curve 825 represents the response to an applied and released elongation during the second cycle. The force relaxation of the web during the first cycle 821 and the degree of set of the web after the first cycle 822 are depicted in FIG. 13. Note that this sample displays very significant elastic recovery over this observed range of elongation as evidenced by the small amount of permanent set 822.

Figure 14:
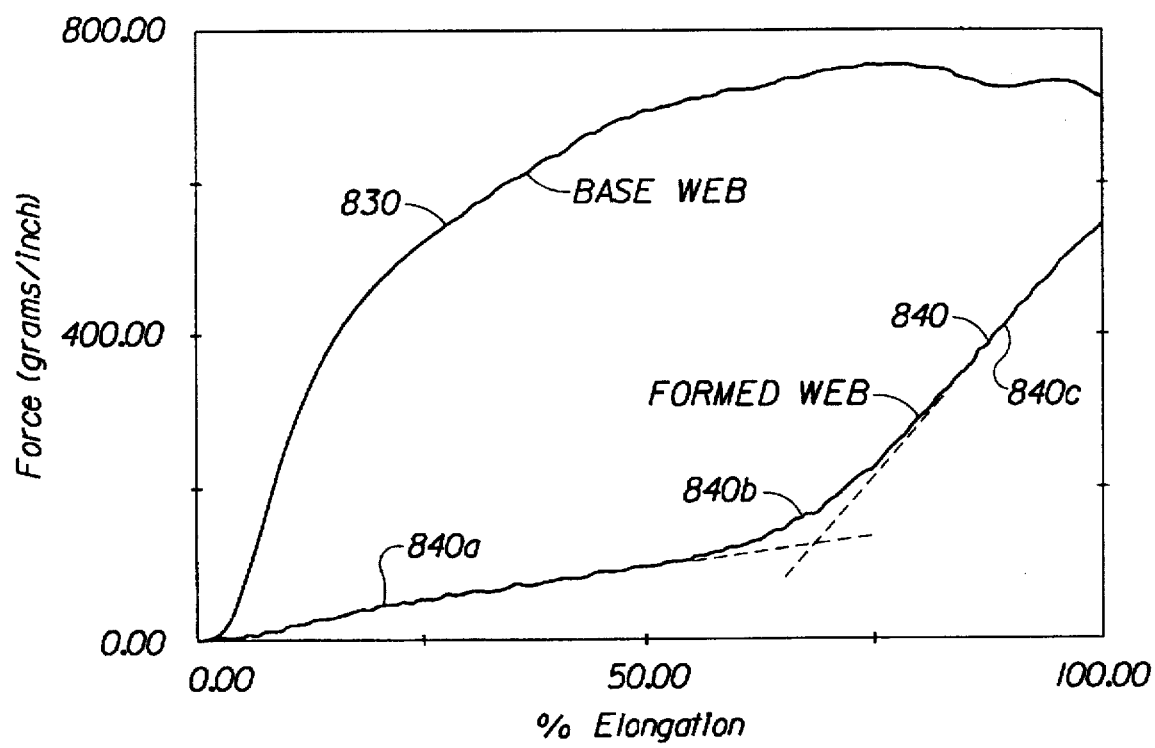
FIG. 14 is a graph of the resistive force versus percent elongation comparing the behavior of another web material of the present invention formed from a laminate comprised of layer of the Clopay 1401 film, Findley adhesive 2301, and a Veratec P-11 nonwoven layer, with a base web of similar material composition.
Figure 15:
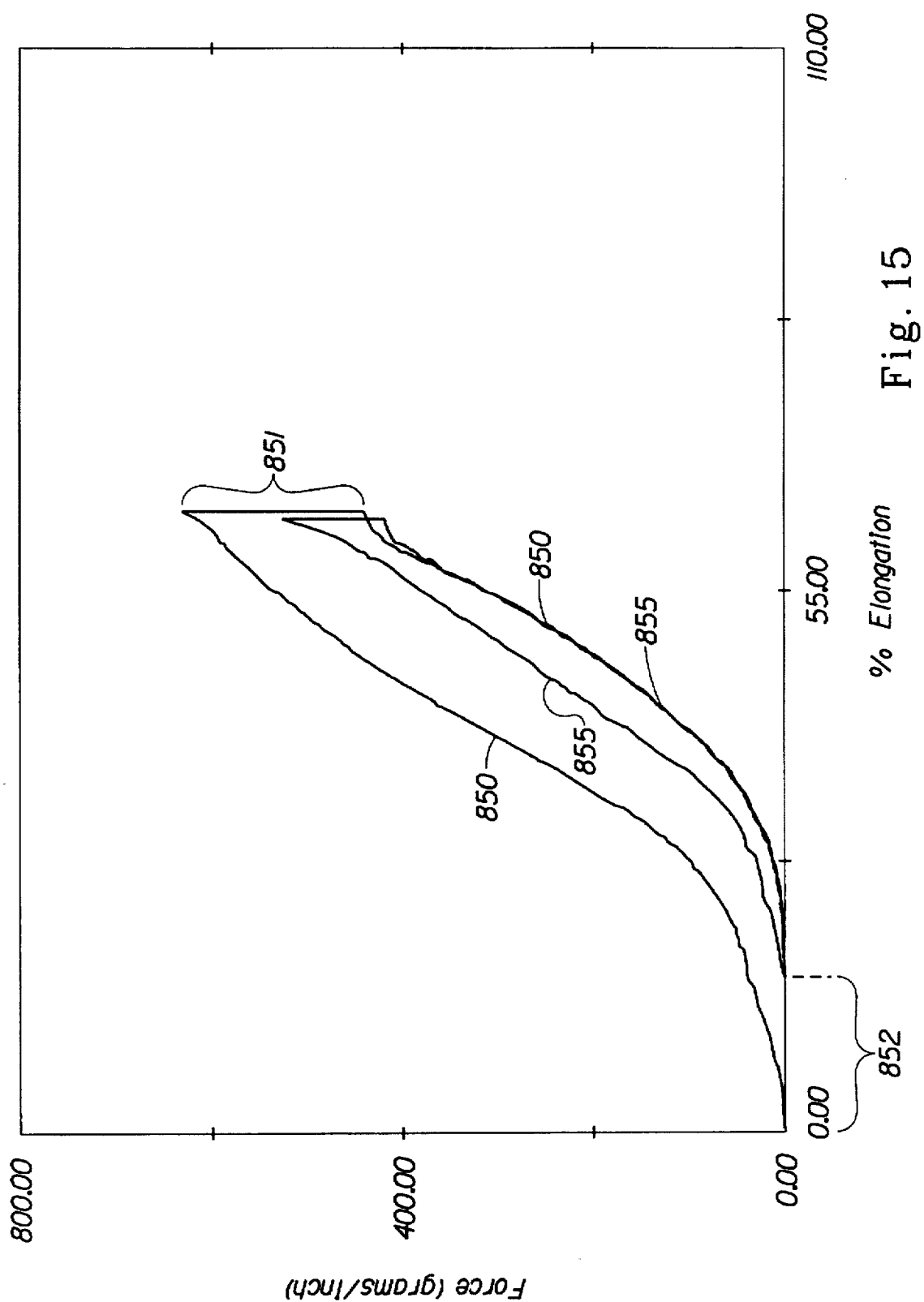
FIG. 15 is a graph of the elastic hysteresis behavior of the web material of the present invention which is graphically represented by curve 840 in FIG. 14 when the web material is subjected to a hysteresis test at 60% elongation.

FIG. 14 shows the force-elongation behavior for both a base web depicted by curve 830 and a formed web of the present invention depicted by curve 840 where both webs are comprised of a laminate of a layer of the Clopay 1401 polyethylene blend film adhered via a hot melt glue available from Findley Adhesives, Wauwatosa, Wis., sample 2301, to a layer of nonwoven layer, made substantially of polypropylene, available from Veratec, Wolpole, Mass., designated type P-11. Referring now to curve 840, there is an initial substantially linear, lower force-elongation stage I designated 840a, a transition zone designated 840b, and a substantially linear stage II designated 840c. For the laminate web, note the distinctive lower force two-stage behavior in the formed web provided first in stage I (840a) by the combination of molecular-level deformation of the first region and geometric deformation of the second region and then in stage II (840c) by molecular-level deformation of both the first region and the second region as depicted in curve 840 compared to the molecular-level deformation of the base web as depicted in curve 830. The curves 850 and 855 in FIG. 15 show the elastic hysteresis behavior of a formed web material similar to that used to generate curve 840 in FIG. 14 examined at 60% elongation. Curve 850 represents the response to an applied and released elongation during the first cycle and curve 855 represents the response to an applied and released elongation during the second cycle. The force relaxation of the web during the first cycle 851 and the percent set of the web after the first cycle 852 are shown in FIG. 15. Note that this laminate web exhibits a very significant elastic recovery over the observed range of elongation over multiple-cycles.

When the web material is subjected to an applied elongation, the web material exhibits an elastic-like behavior as it extends in the direction of applied elongation and returns to its substantially untensioned condition once the applied elongation is removed, unless the web material is extended beyond the point of yielding. The web material is able to undergo multiple cycles of applied elongation without losing its ability to substantially recover. Accordingly, the web is able to return to its substantially untensioned condition once the applied elongation is removed.

While the web material may be easily and reversibly extended in the direction of applied axial elongation, in a direction substantially perpendicular to the first axis of the rib-like elements, the web material is not as easily extended in a direction substantially parallel to the first axis of the rib-like elements. The formation of the rib-like elements allows the rib-like elements to geometrically deform in a direction substantially perpendicular to the first or major axis of the rib-like elements, while requiring substantially molecular-level deformation to extend in a direction substantially parallel to the first axis of the rib-like elements.

The amount of applied force required to extend the web is dependent upon the composition and cross-section area of the web material and the width and spacing of the first regions, with narrower and more widely spaced first regions requiring lower applied extensional forces to achieve the desired elongation for a given composition and cross-sectional area. The first axis, (i.e., the length) of the first regions is preferably greater than the second axis, (i.e., the width) of the first regions with a preferred length to width ratio of from about 5:1 or greater.

The depth and frequency of rib-like elements can also be varied to control the available stretch of a web of the present invention. The available stretch is increased if for a given frequency of rib-like elements, the height or degree of formation imparted on the rib-like elements is increased. Similarly, the available stretch is increased if for a given height or degree of formation, the frequency of the rib-like elements is increased.

While the particular web material 52 of FIG. 5 is an example of an elastic-like web of the present invention, the present invention is not limited to the geometric formation shown in web material 52. FIGS. 16–28 depict several alternative embodiments of web materials of the present invention.

There are several functional properties that can be controlled through the application of the present invention. The functional properties are the resistive force exerted by the web material against an applied elongation and the available stretch of the web material before the force wall is encountered. The resistive force that is exerted by the web material against an applied elongation is a function of the material (e.g., composition, molecular structure and orientation, etc.) and cross-sectional area and the percent of the projected surface area of the web material that is occupied by the first region. The higher the percent area coverage of the web material by the first region, the higher the resistive force that the web will exert against an applied elongation for a given material composition and cross-sectional area. The percent coverage of the web material by the first region is determined in part if not wholly by the widths of the first regions and the spacing between adjacent first regions.

The available stretch of the web material is determined by the surface-pathlength of the second region. This is determined at least in part by the rib-like element spacing, rib-like element frequency and depth of formation of the rib-like elements as measured perpendicular to the plane of the web material. In general, the greater the surface-pathlength of the second region the greater the available stretch of the web material.

Figure 16:
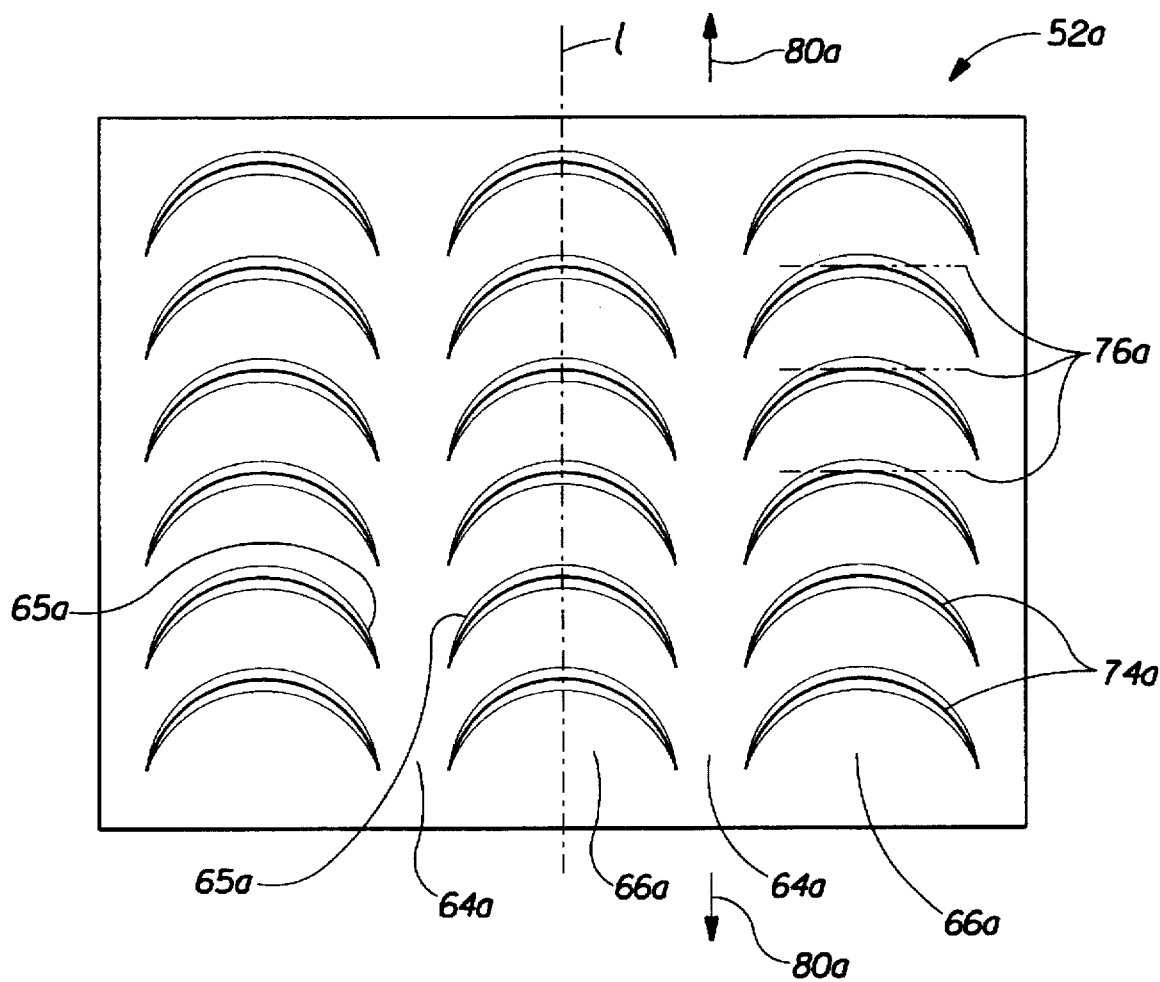
FIGS. 16–29 are illustrations of other preferred embodiments of web materials of the present invention.
Figure 17:
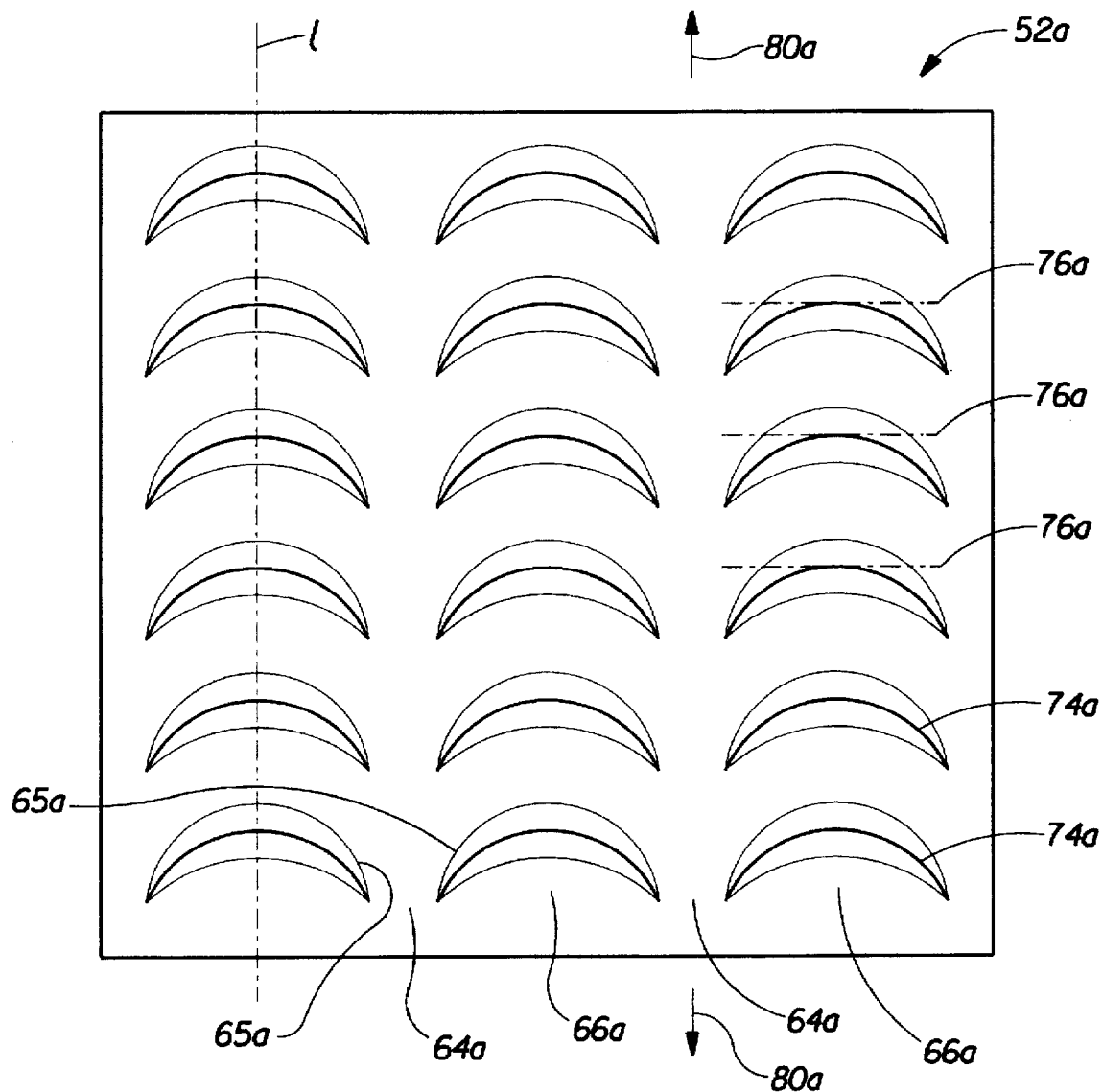

In FIG. 16 there is shown a formed web material 52a of the present invention in an untensioned condition which contains first regions 64a and second regions 66a. Web material 52a also includes transitional regions 65a located intermediate first regions 64a and second regions 66a. The web material 52a will exhibit an elastic-like behavior in response to an applied cyclical elongation in a direction along an axis indicated as "l". Second regions 66a contain curvilinear rib-like elements 74a. The first or major axis 76a of the curvilinear rib-like elements 74a is a linear approximation of the rib-like element 74a. The major axis 76a defines that portion of the rib-like element 74a which substantially responds to an applied elongation via geometric deformation. In FIG. 17 there is shown the same web material of FIG. 16 in a tensioned condition. The tension in the web material, as a result of the applied elongation indicated by arrows 80a causes the geometric deformation of rib-like elements 74a in a direction perpendicular to the first axis 76a due to the unbending of the rib-like elements 74a.

Figure 18:
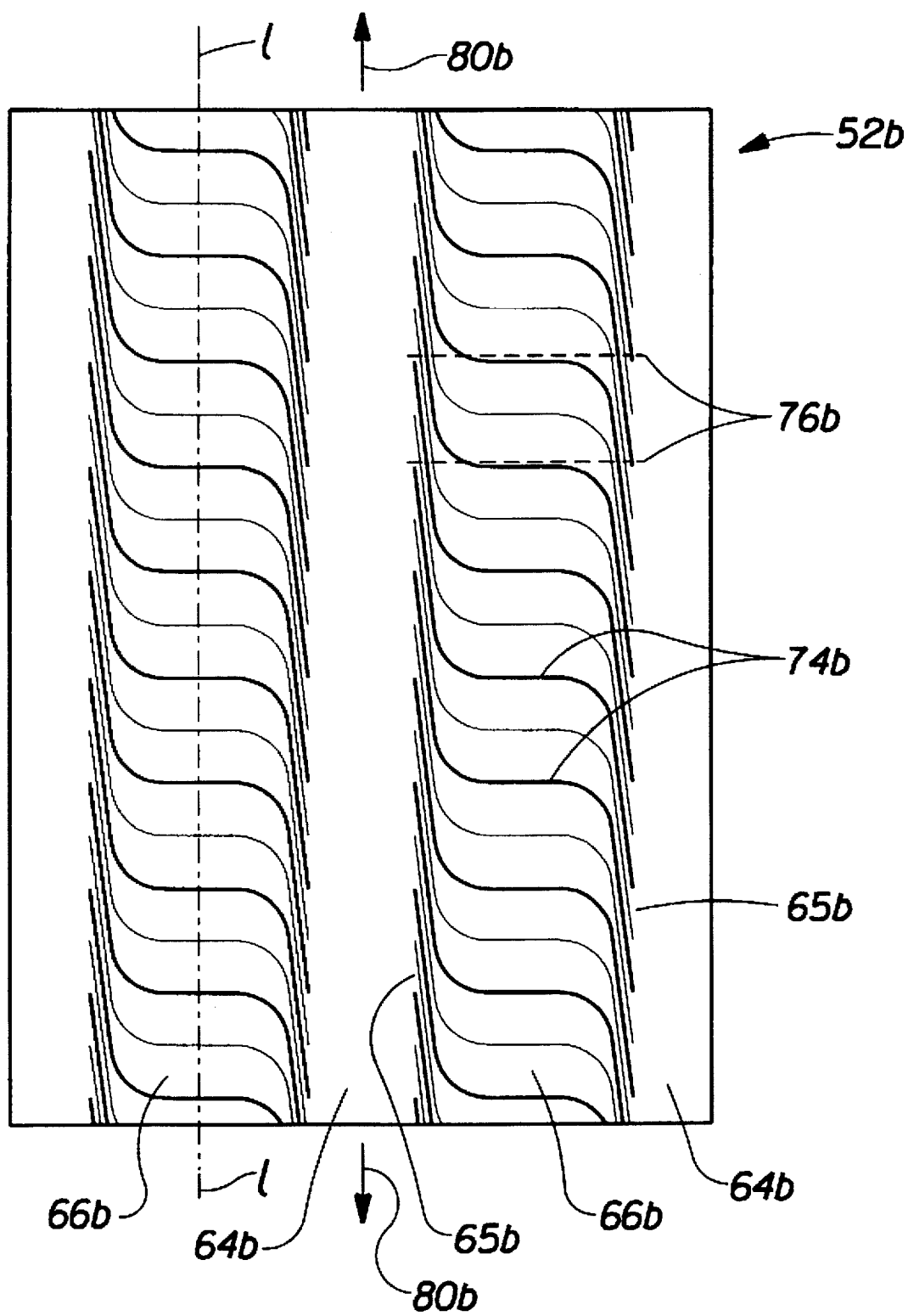
Figure 19:
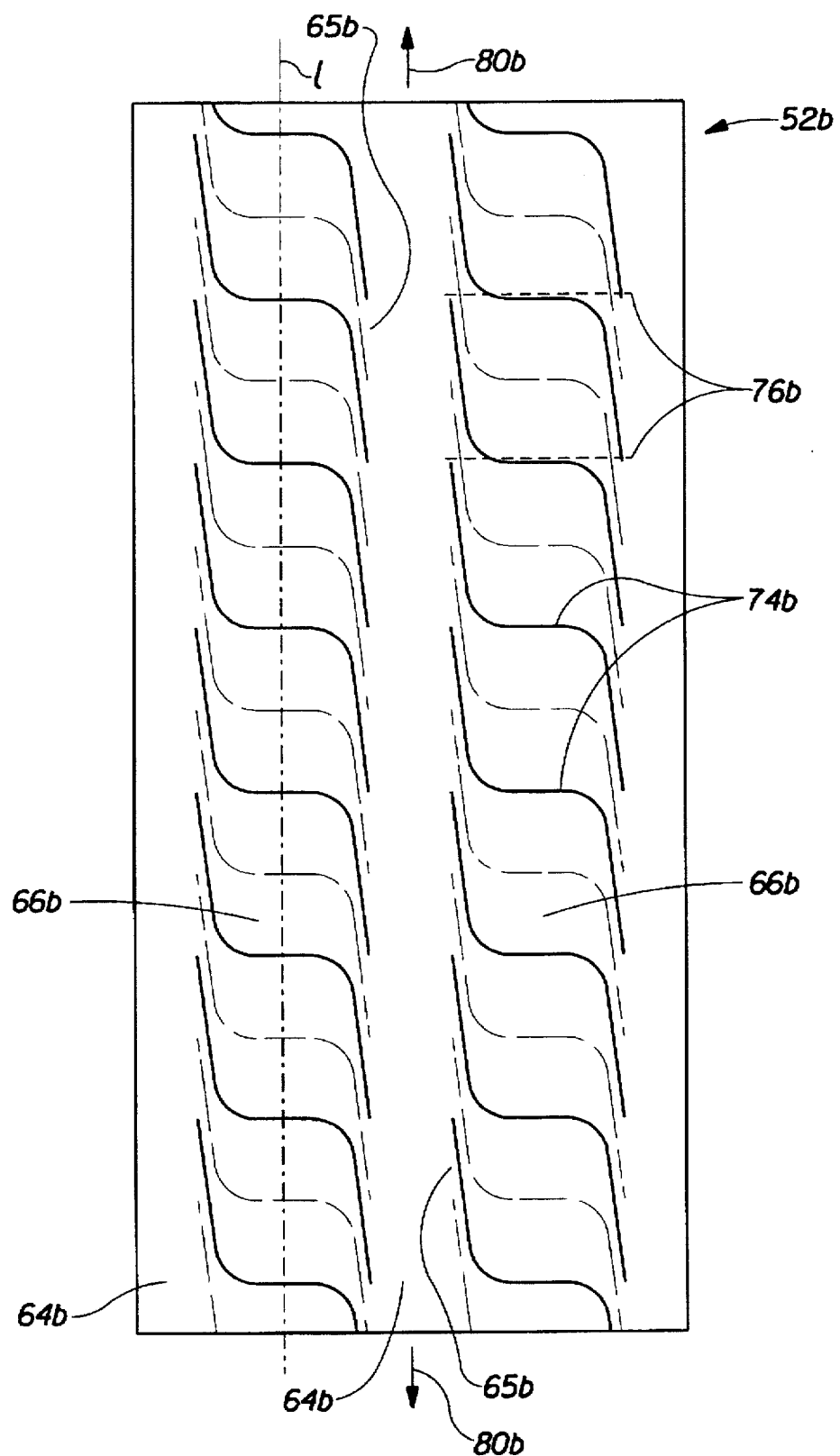

In FIG. 18 there is shown a formed web material 52b of the present invention in an untensioned condition which contains first regions 64b and second regions 66b. Web material 52b also includes transition regions 65b located intermediate first regions 64b and second regions 66b. The web material 52b will exhibit an elastic-like behavior in response to an applied cyclical elongation in a direction along an axis indicated as "l". Second regions 66b contain complex shaped rib-like elements 74b. The first or major axis 76b of the rib-like elements 74b are a linear approximation of the rib-like elements 74b. The first or major axis 76b defines that portion of the rib-like element 74b which substantially responds to an applied elongation via geometric deformation. In FIG. 19 there is shown the same formed web material of FIG. 18 in a tensioned condition. The tension in the web material shows the geometric deformation of rib-like elements 74b perpendicular to the major axis 76b due to unbending of the rib-like elements 74b as a result of the applied elongation indicated by arrows 80b.

Figure 20:
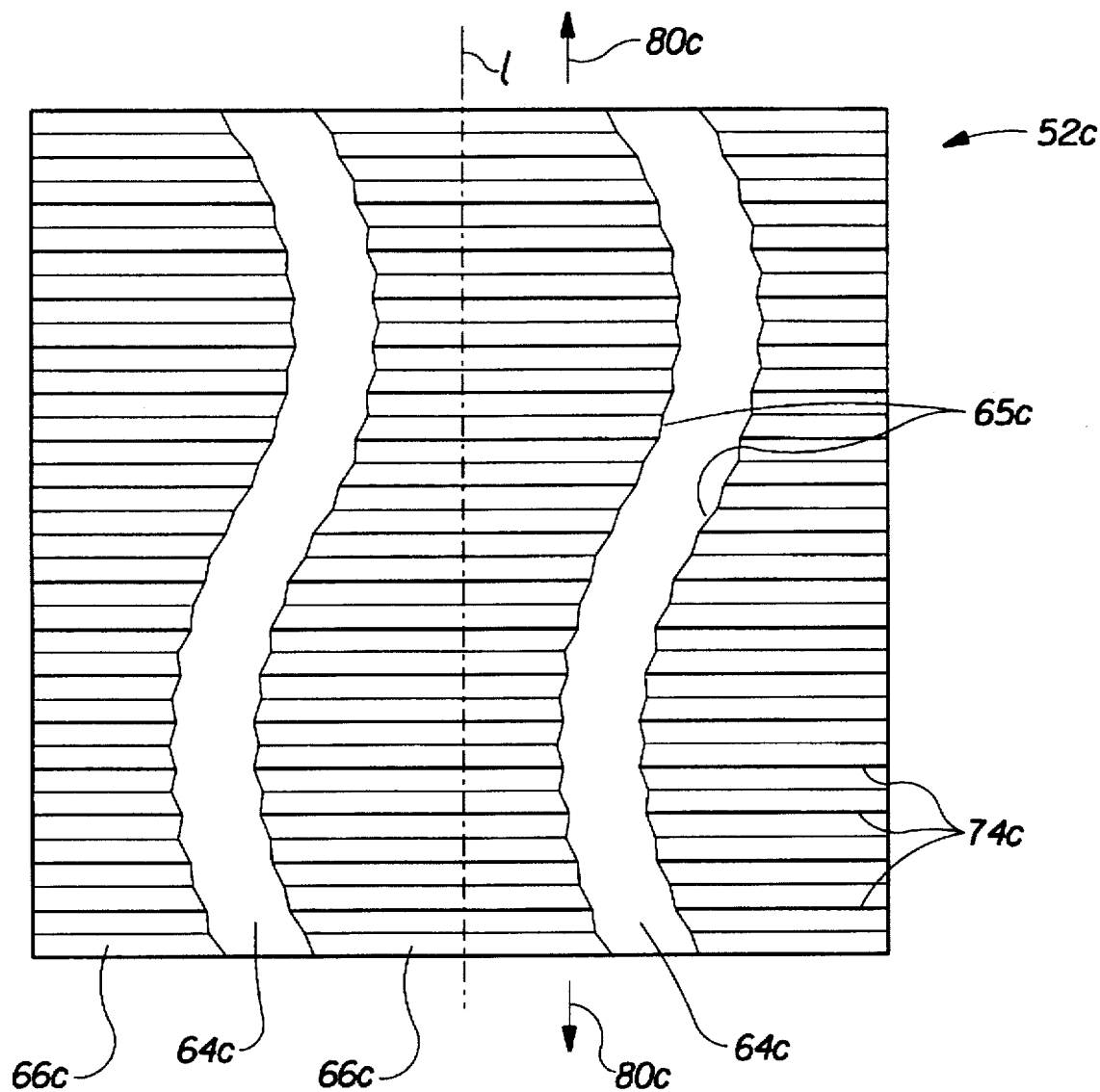

In FIG. 20 there is shown another embodiment of a formed web material 52c of the present invention in the untensioned condition. Web material 52c contains first regions 64c and second regions 66c. Web material 52c also includes transitional regions 65c located intermediate first regions 64c and second regions 66c. The web material 52c will exhibit an elastic-like behavior in response to an applied cyclical elongation in a direction along an axis indicated as "l". Second region 66c contains rib-like elements 74c. The first regions 64c and the second regions 66c are curvilinear. First regions will undergo a substantially molecular-level deformation while the second regions will initially undergo a substantially geometric deformation when the formed web material 52c is subjected to an applied elongation indicated by arrows 80c.

Figure 21:
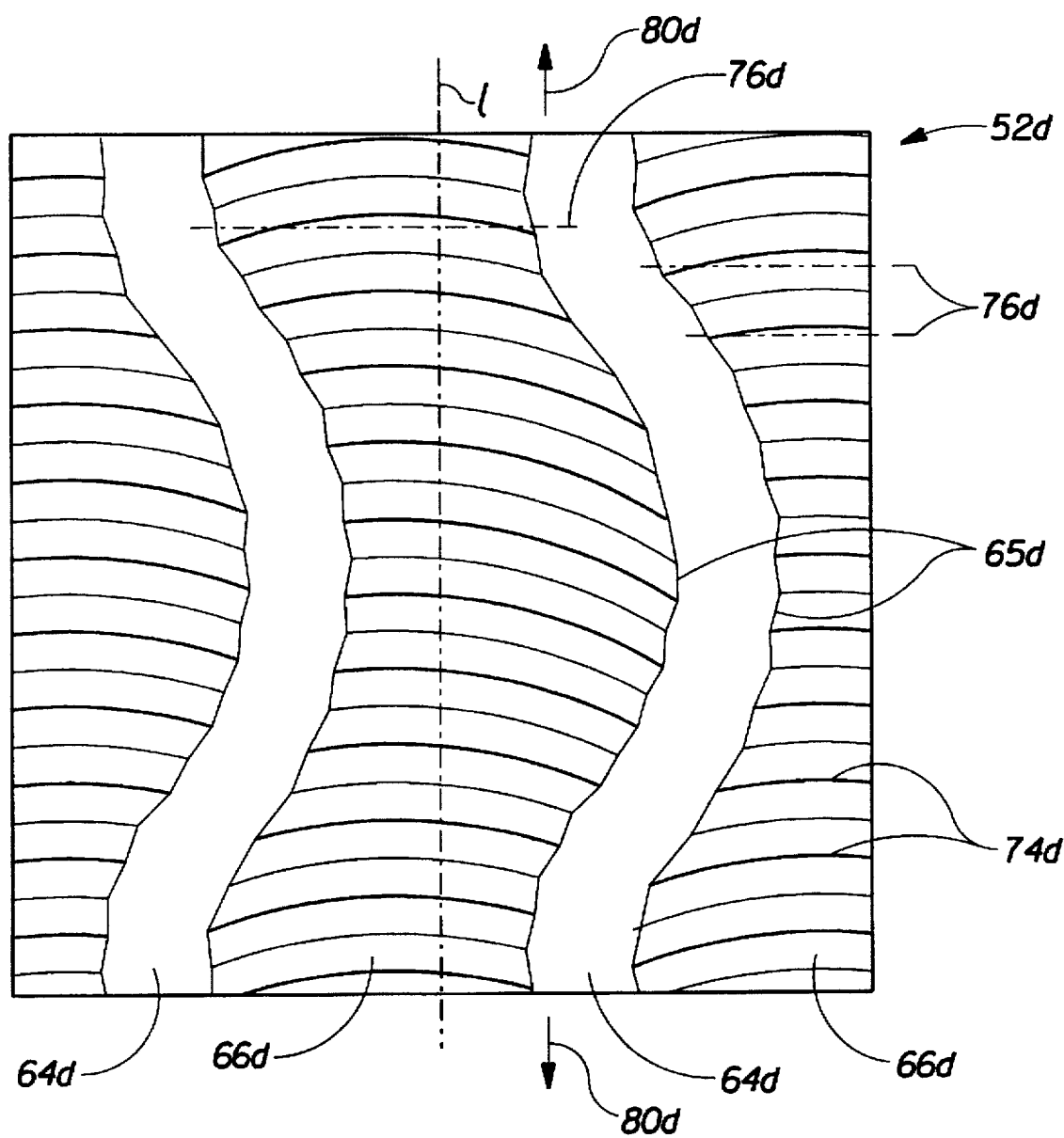

In FIG. 21 there is shown another embodiment of a formed web material 52d of the present invention in an untensioned condition. Web material 52d contains first regions 64d and second regions 66d. Web material 52d also includes transitional regions 65d located intermediate first regions 64d and second regions 66d. Second regions 66d contain curvilinear rib-like elements 74d. The major axis 76d of the curvilinear rib-like elements 74d is a linear approximation of the rib-like elements 74d. The major axis 76d defines that portion of the rib-like elements 74d which substantially responds to an applied elongation via geometric deformation. The web material 52d will exhibit an elastic-like behavior in response to an applied cyclical elongation in a direction along an axis indicated as "l". The first regions undergo a substantially molecular-level deformation and the second regions initially undergo a substantially geometric deformation when the formed web material 52d is subjected to an applied elongation indicated by arrows 80d.

Figure 22:
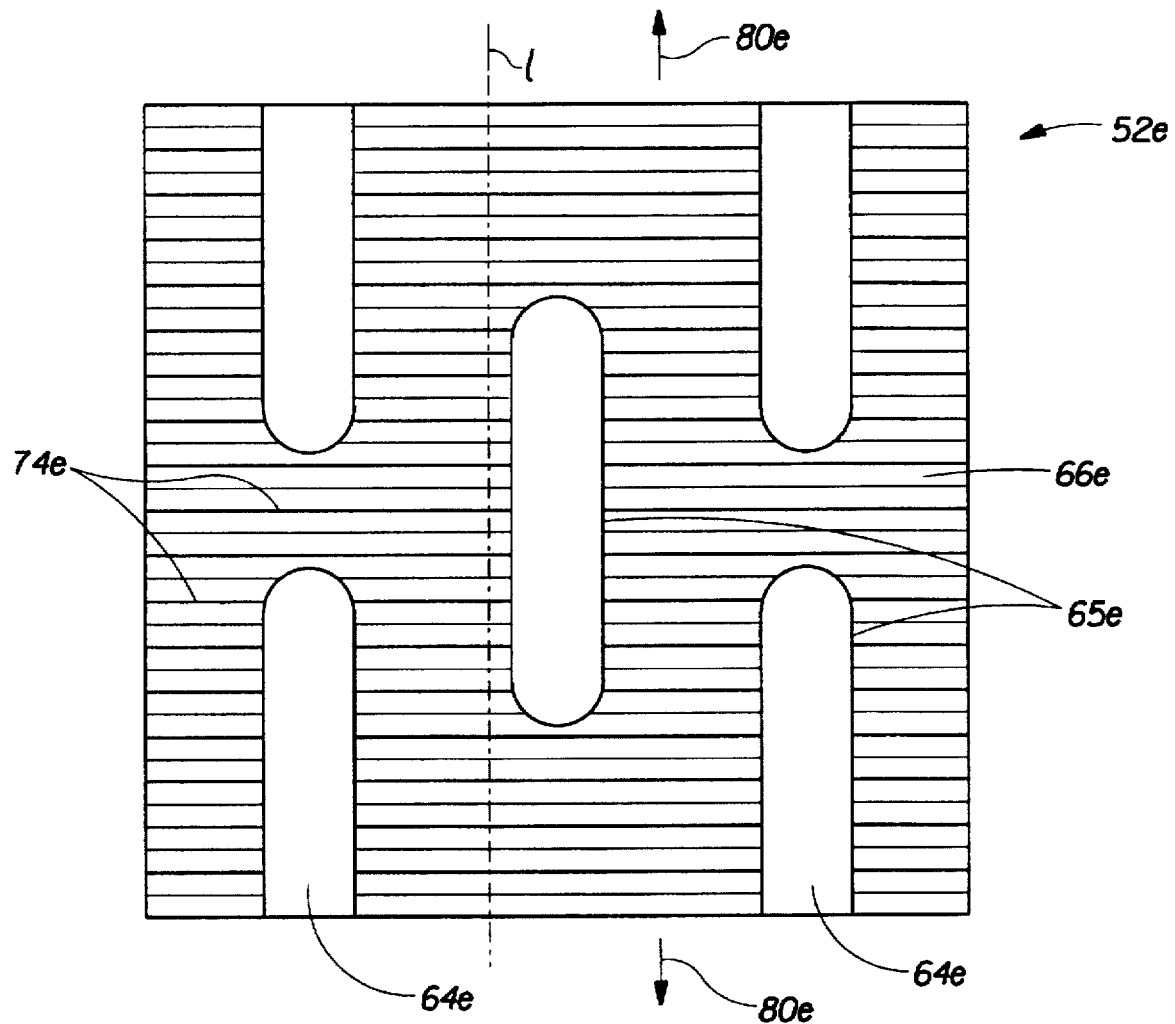

In FIG. 22 there is shown a web material 52e of the present invention in an untensioned condition which contains first regions 64e and second regions 66e. Web material 52e also includes transitional regions 65e located intermediate first regions 64e and second regions 66e. Second regions 66e contain rib-like elements 74e. The first regions 64e are discontinuous throughout the length of the web material. The web material 52e will exhibit an elastic-like behavior in response to an applied cyclical elongation indicated by arrows 80e in a direction substantially parallel to axis "l".

Figure 23:
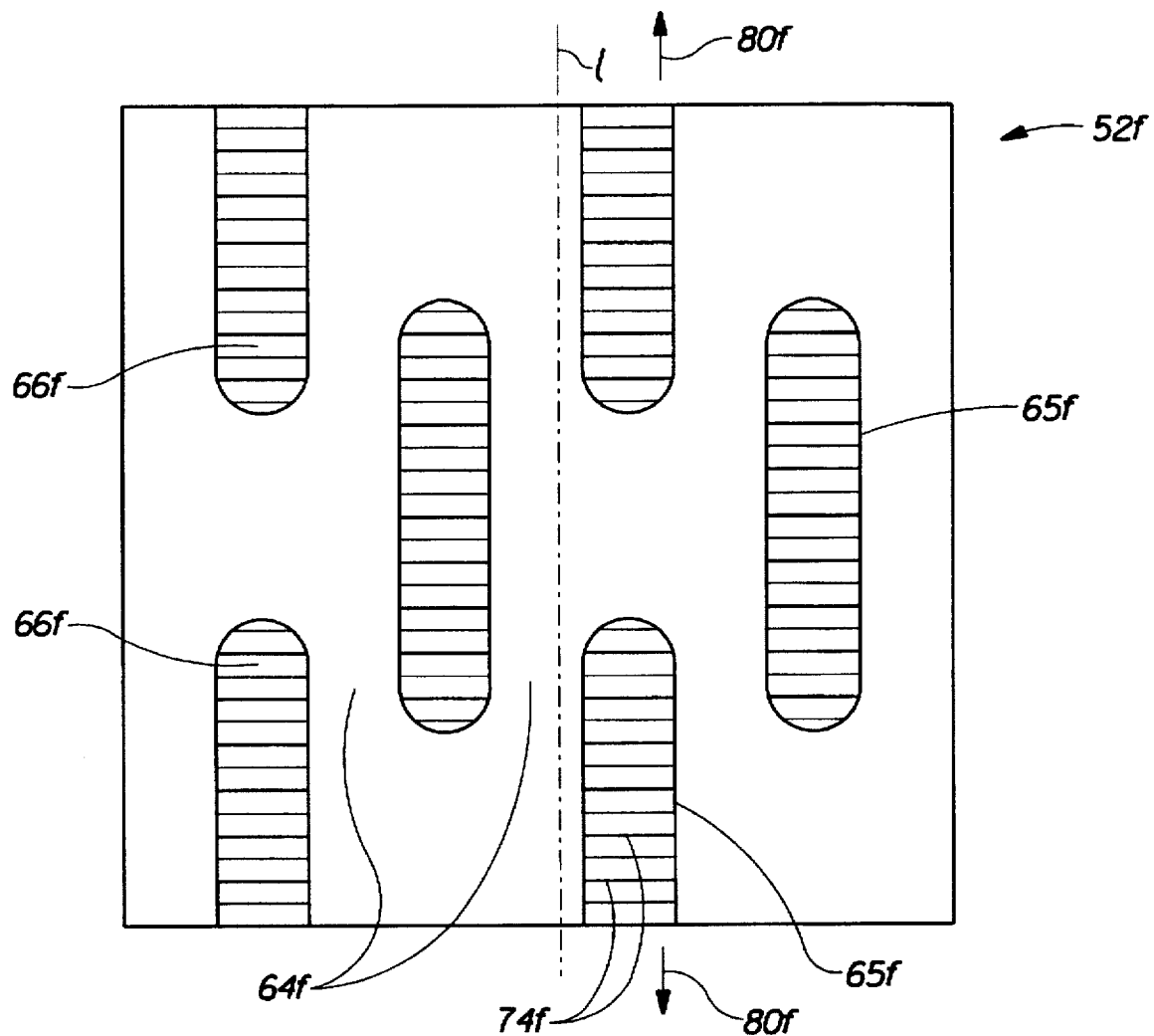

In FIG. 23 there is shown a web material 52f of the present invention in an untensioned condition which contains first regions 64f and second regions 66f. Web material 52f also includes transitional regions 65f located intermediate first regions 64f and second regions 66f. Second regions 66f contain rib-like elements 74f. The first regions 64f extend continuously throughout the length of the web material while the second regions 66f are discontinuous or interrupted. The web material of 52f will exhibit an elastic-like behavior in response to an applied cyclical elongation indicated by arrows 80f in a direction substantially parallel to axis "l".

Figure 24:
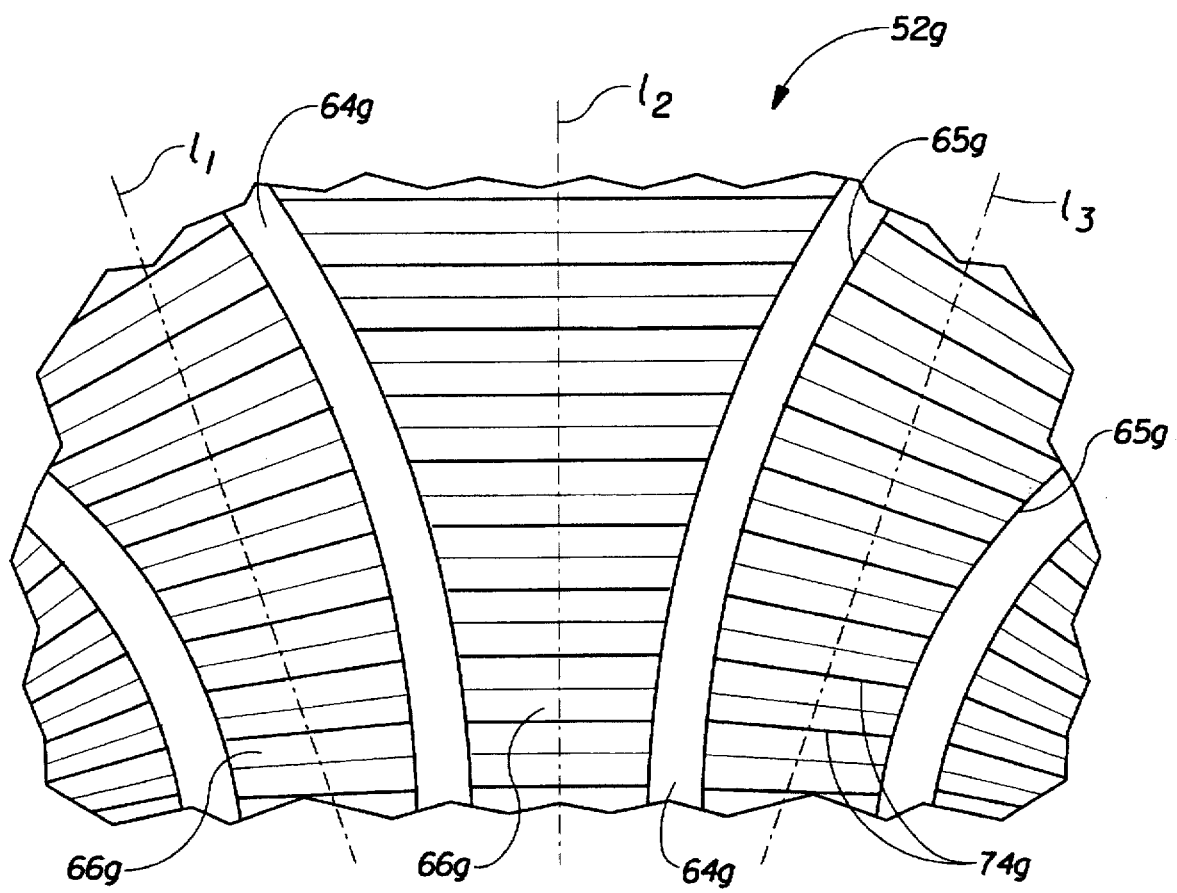

In FIG. 24 there is shown a formed web material 52g of the present invention in an untensioned condition. Web material 52g contains first regions 64g and second regions 66g. Web material 52g also includes transitional regions 65g located intermediate first regions 64g and second regions 66g. The second regions 66g contain rib-like elements 74g. The formed web material 52g exhibits an elastic-like behavior along a plurality of axis, "l1", "l2" and "l3". Axes l1, l2, and l3, extend in a radial, fan-like array to allow the formed web material 52g to exhibit an elastic-like behavior along a plurality of axes. While web material 52g has been shown as having axes extending in a fan-like array, the present invention is in no way limited to such. The multiple axes may be positioned at various angles to one another such as 45°, 90°, 135°, etc. In addition to the various angles of orientation, the regions themselves may be straight, curvilinear, or combinations thereof.

Figure 25:
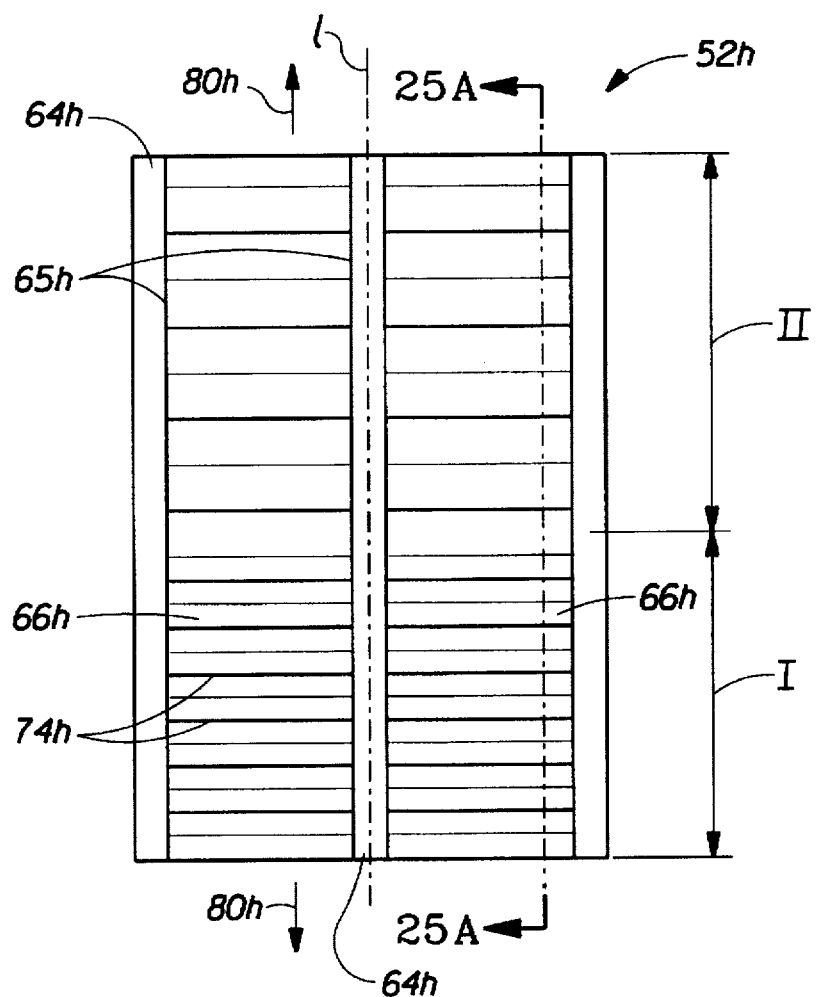
Figure 25A:
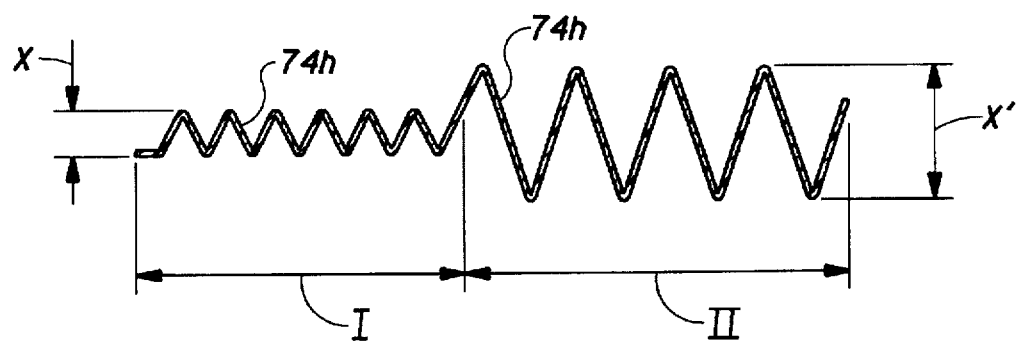

In FIG. 25 there is shown a formed web material 52h of the present invention. Web material 52h includes first regions 64h and second regions 66h. Web material 52h also includes transitional regions 65h located intermediate first regions 64h and second regions 66h. Second region 66h includes a plurality of rib-like elements 74h. In FIG. 25A there is shown a cross-sectional view of the second region 66h taken along section-line 25A—25A depicting the amplitudes x and x' of the rib-like elements 74h. The surface-pathlength of zone I in second region 66h will be substantially less than the surface-pathlength of zone II in second region 66h at least due in part to a difference in amplitudes x and x' of the rib-like elements 74h in the respective zones. As web material 52h is subjected to an applied elongation indicated by arrows 80h in a direction substantially parallel to axis "l", web material will have different zones of available stretch corresponding to zones I and II in the second regions 66h. Specifically, the available stretch of web 52h corresponding to zone I will be less than the available stretch of web material 52h corresponding to zone II. However, while the available stretch for zones I and II are different from one another, web material 52h will not encounter a force wall until the available stretch for both zones I and II has been reached.

Figure 26:
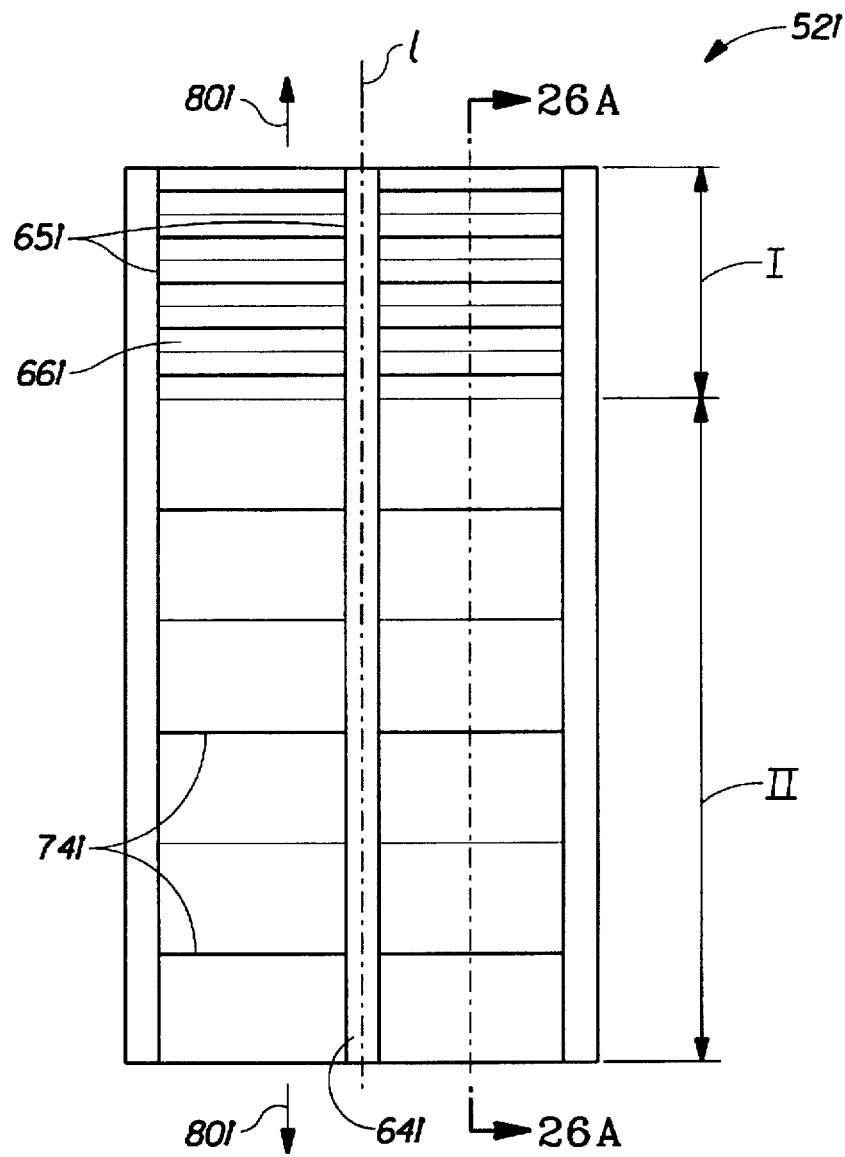
Figure 26A:
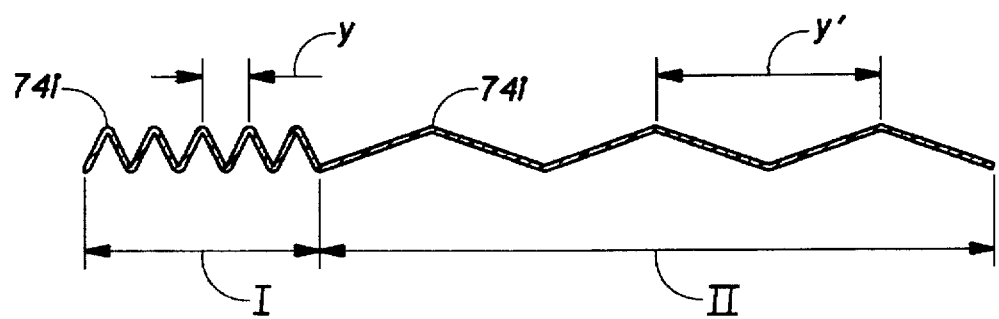

In FIG. 26 there is shown a formed web material 52i of the present invention. Web material 52i includes first regions 64i and second regions 66i. Web material 52i also includes transitional regions 65i located intermediate first regions 64i and second regions 66i. Second regions 66i include rib-like elements 74i. FIG. 26A is a cross-sectional view of the second region 66i taken along section line 26A—26A depicting the frequencies y and y' of the rib-like elements 74i. Due to the difference in surface-pathlengths in zones I and II web material 52i of FIGS. 26 and 26A will respond to an applied and released elongation similar to web 52h depicted in FIGS. 25 and 25A.

While the web materials in FIGS. 25 and 26 illustrate variations in the rib-like elements within a second region one could also vary the rib-like elements between adjacent regions. The variations in rib-like elements in adjacent second regions provides different available stretches in the adjacent second regions. By having different available stretches in adjacent second regions the web material will exhibit multiple force walls in response to an applied elongation as each region reaches its limit of geometric deformation.

Figure 27:
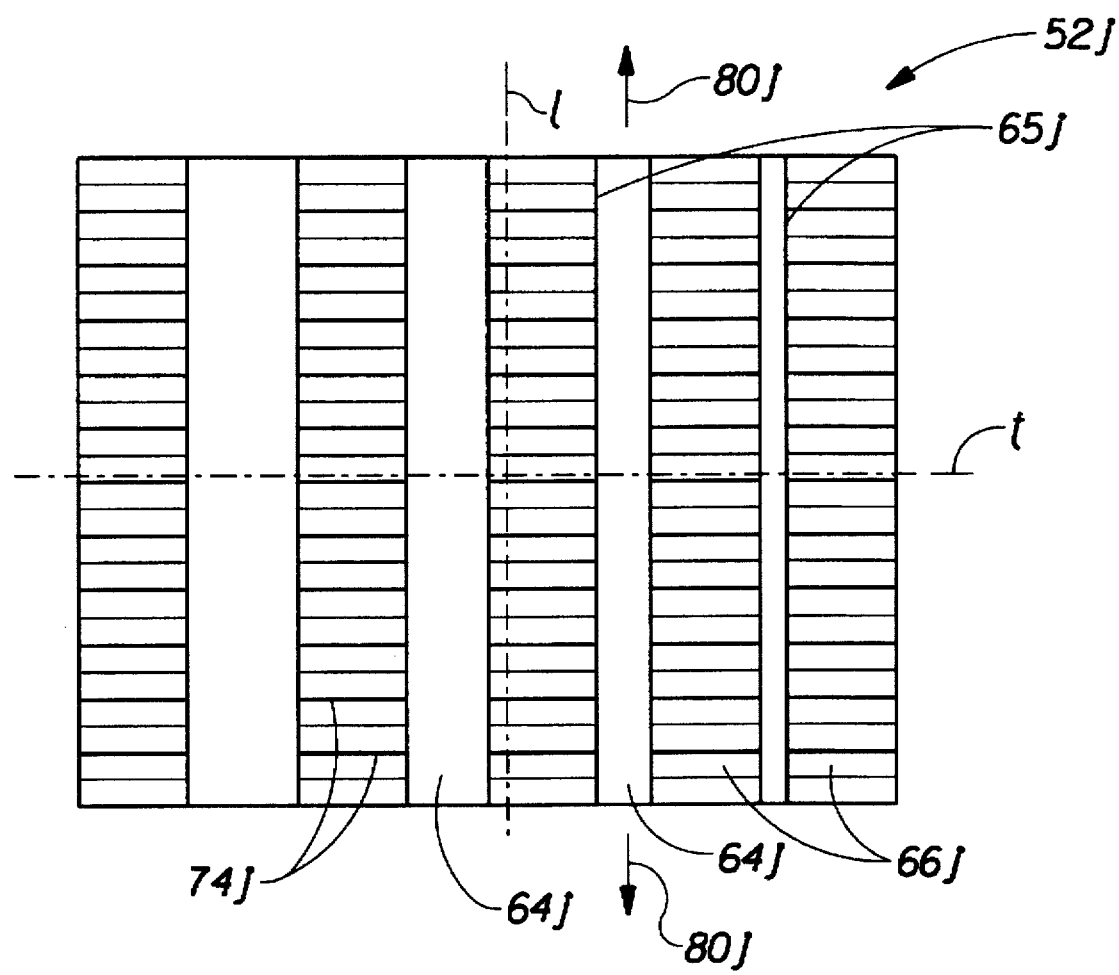

In FIG. 27 there is shown another embodiment of a formed web material 52j of the present invention. Web material 52j includes first regions 64j and second regions 66j. Web material 52j also includes transitional regions 65j located intermediate first regions 64j and second regions 66j. The widths of the first regions 64 varies across the web in a direction substantially parallel to the axis "t". Second regions 66j include a plurality of rib-like elements 74j. As the web material 52j is subjected to an applied elongation indicated by arrows 80j in a direction substantially parallel to the axis "l", the narrower regions 64 will offer a lower resistive force to the applied elongation as compared to the higher resistive force offered by the wider first regions 64j.

Figure 28:
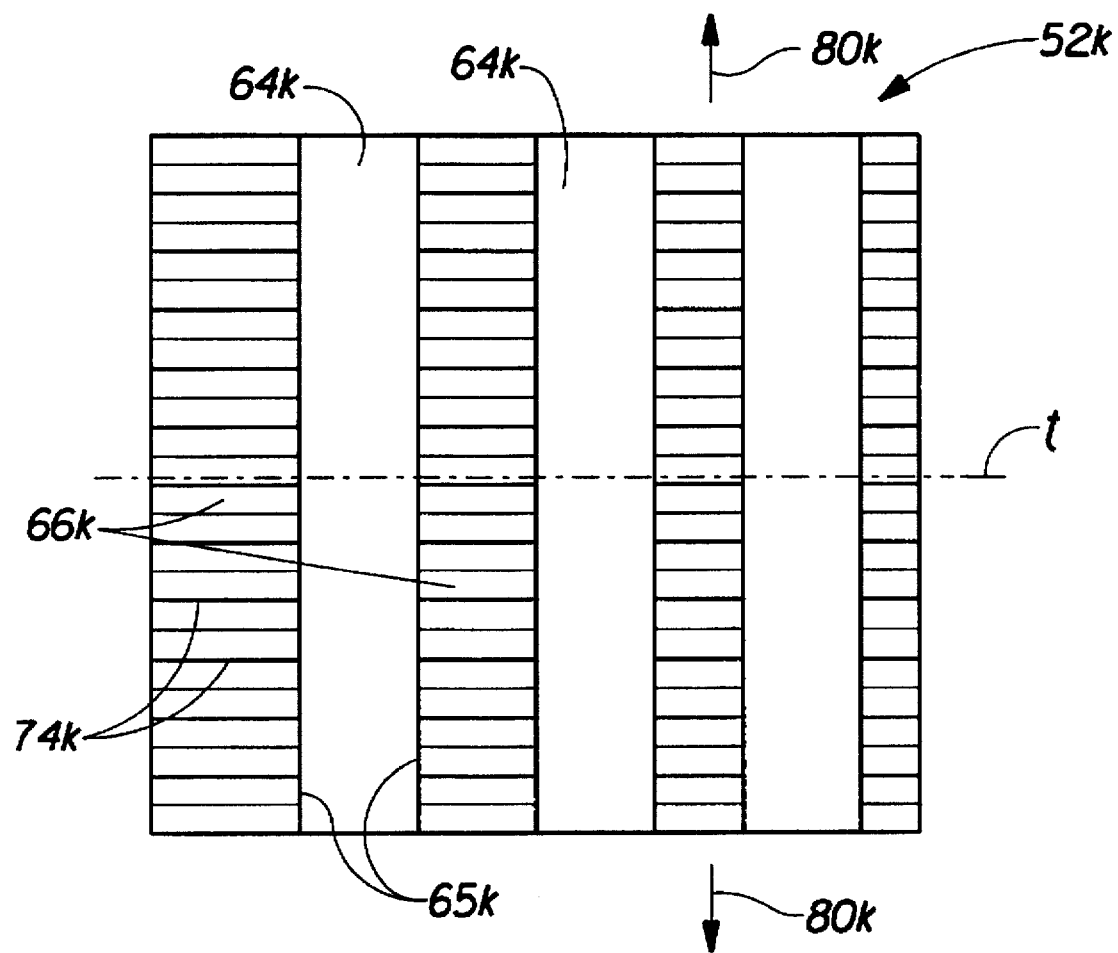

In FIG. 28 there is shown another embodiment of a formed web material 52k of the present invention. Web material 52k includes first regions 64k and second regions 66k. Web material 52k also includes transitional regions 65k located intermediate first regions 64k and second regions 66k. Second regions 66k include rib-like elements 74k. The widths of the second regions 66k varies across the web in a direction substantially parallel to axis "t". When subjected to an applied elongation indicated by arrows 80k in a direction substantially parallel to axis "l" the portions of the web material 52k having the wider second regions 66k will provide a lower resistive force to the applied elongation as compared to the portion of web material 52k having the narrower second regions 66k. It should be obvious to one skilled in the art that the features of the web materials disclosed in FIGS. 27 and 28 can be combined in a single web to provide various resistive forces to applied elongations.

Figure 29:
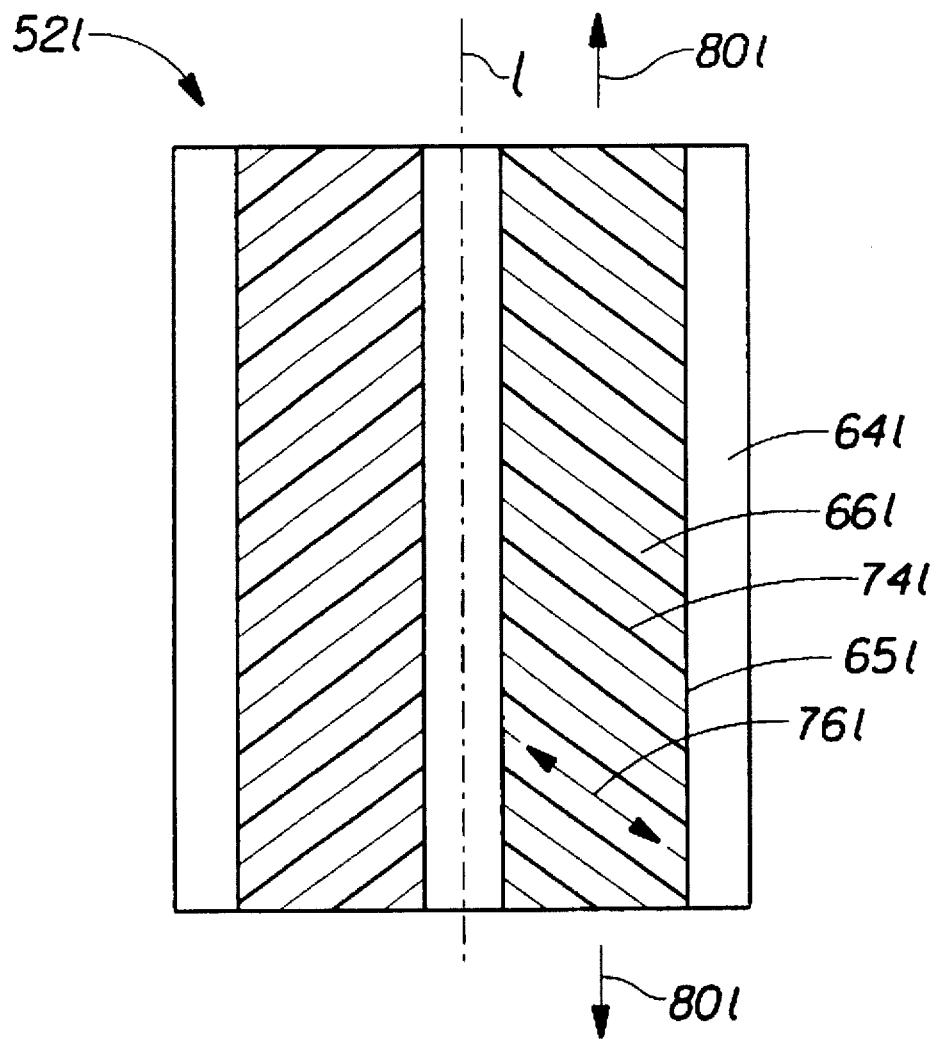

In FIG. 29 there is shown another embodiment of a web material 521 of the present invention. Web material 521 includes first regions 641 and second regions 661. Web material 521 also includes transitional regions 651 located intermediate first regions 641 and second regions 661. Second regions 661 include rib-like elements 741. Second regions 661 extend in a direction substantially parallel to axis "l". The major axis 761 of the rib-like elements 741 extends at a slight angle to axis "l" but is still substantially perpendicular to axis "l". As the web material 521 is subjected to an applied elongation indicated by arrows 801 in a direction substantially parallel to axis "l" rib-like elements 741 will geometrically deform at least in part by pivoting in response to the applied elongation. The pivoting of rib-like elements 741 may cause the rib-like elements 741 to become aligned substantially parallel with the axis "l".

Figure 30:
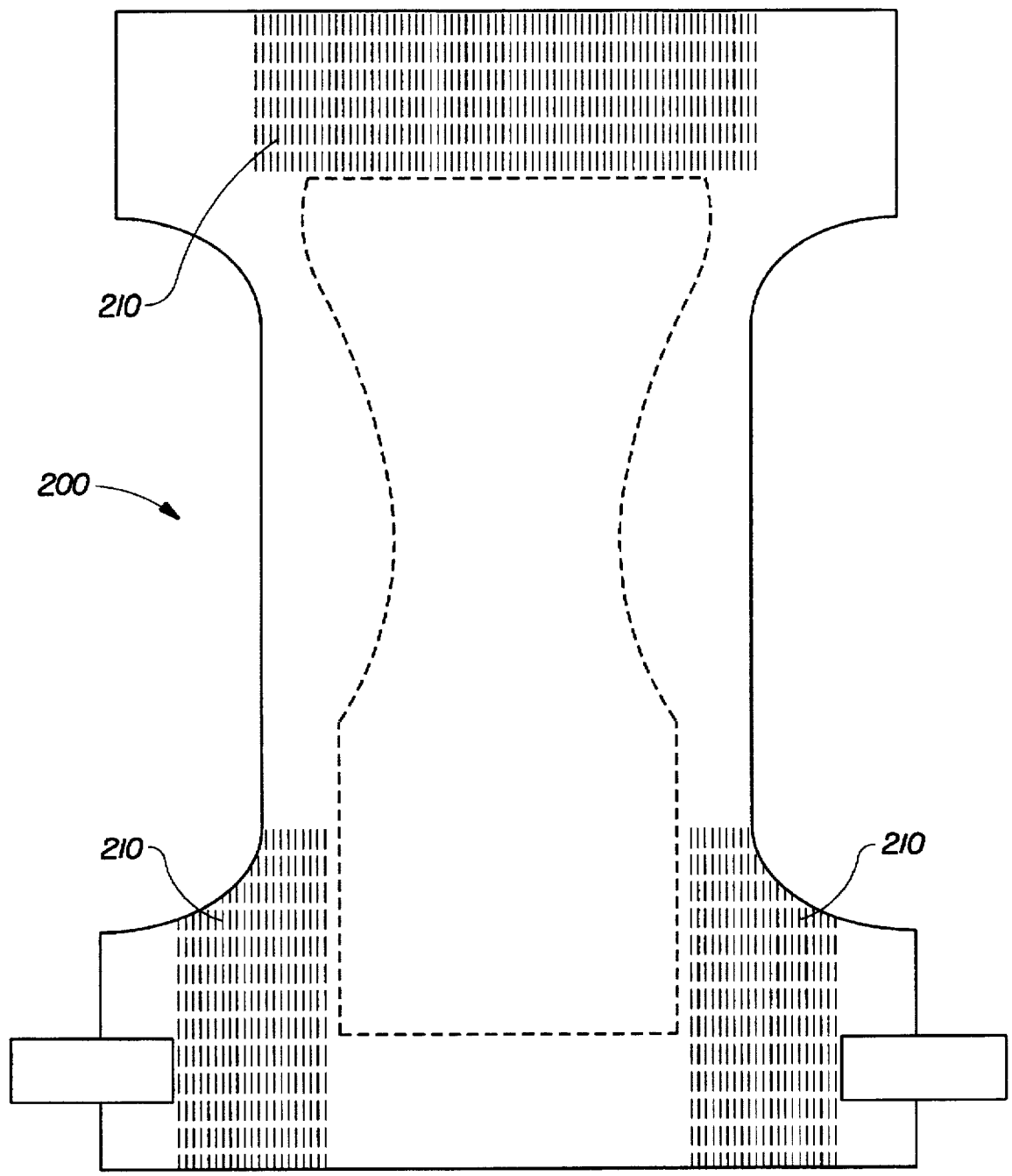
FIG. 30 is a plan view illustration of a disposable diaper backsheet of the present invention.

While an entire web material of the present invention may include a strainable network of first and second regions, the present invention may also be practiced by providing only specific portions of the web with a strainable network comprised of first and second regions. Referring now to FIG. 30, there is shown a preferred embodiment of a disposable diaper backsheet 200 of the present invention, wherein the backsheet 200 includes discrete, strainable networks 210 located in the waist region and the side panels of the disposable diaper backsheet. It will be obvious to one skilled in the art that all or a portion of a backsheet on a disposable absorbent article may include a strainable network(s) comprised of first and second regions to provide a backsheet exhibiting an elastic-like behavior along an axis when subjected to an applied cyclical elongation.

Figure 31:
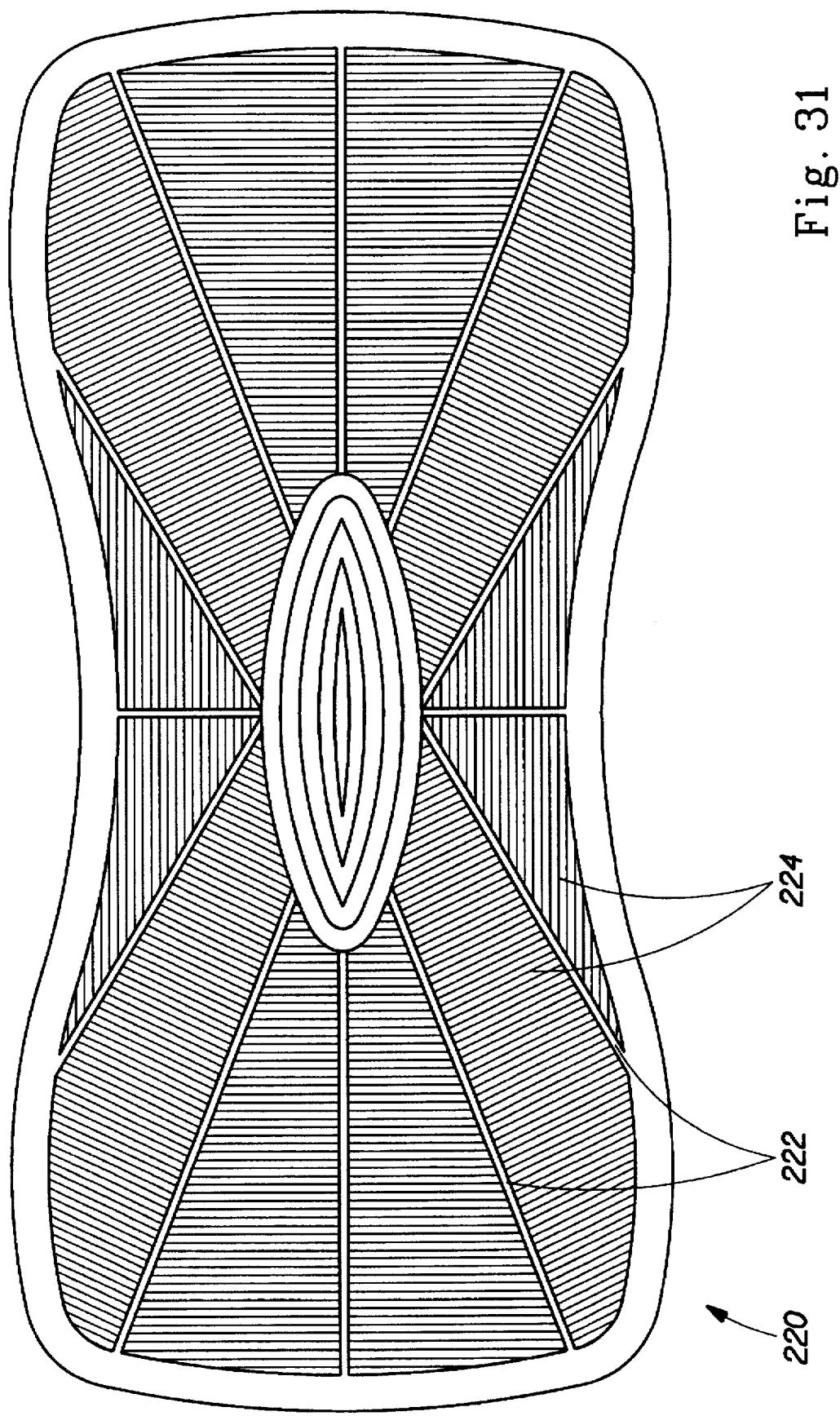
FIG. 31 is a plan view illustration of a sanitary napkin backsheet of the present invention.

Referring now to FIG. 31, there is shown an embodiment of a sanitary napkin backsheet 220. The backsheet 220 includes a plurality of first regions 222 and a plurality of second regions 224 each extending in several different directions. Accordingly, the backsheet 220 is able to exhibit elastic-like behavior in several directions to applied cyclic elongations along a plurality of axes.

While the web material having a strainable network of the present invention has been described as a backsheet or a portion thereof on an absorbent article, in some embodiments it may be necessary to provide the topsheet and the absorbent core with a strainable network. For example, in the embodiment illustrated in FIG. 30, it is necessary to provide the topsheet with a strainable network in regions adjacent backsheet regions 210 to allow region 210 of the backsheet to extend without being restrained by adjacent portions of the topsheet.

Method of Making

Figure 32:
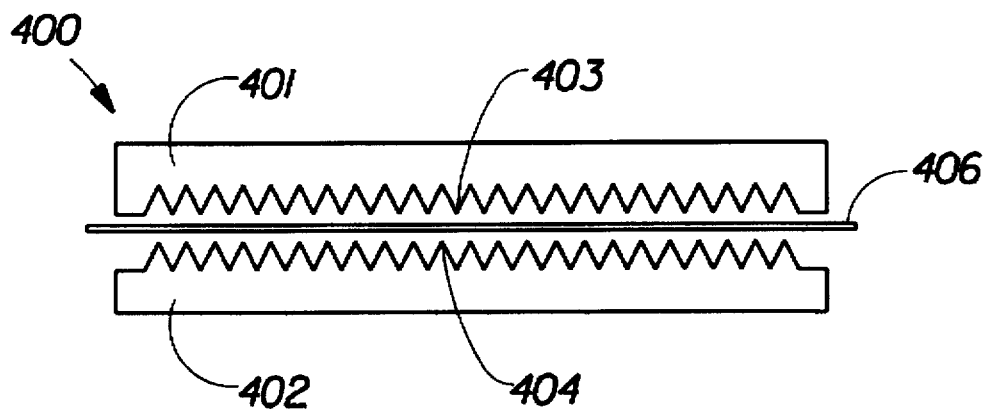
FIG. 32 is a simplified side elevational view of a preferred apparatus used to form web materials of the present invention.

Referring now to FIG. 32, there is shown an apparatus 400 used to form the web 52 shown in FIG. 5. Apparatus 400, includes plates 401, 402. Plates 401, 402 include a plurality of intermeshing teeth 403, 404, respectively. Plates 401, 402 are brought together under pressure to form the base film 406.

Figure 33:
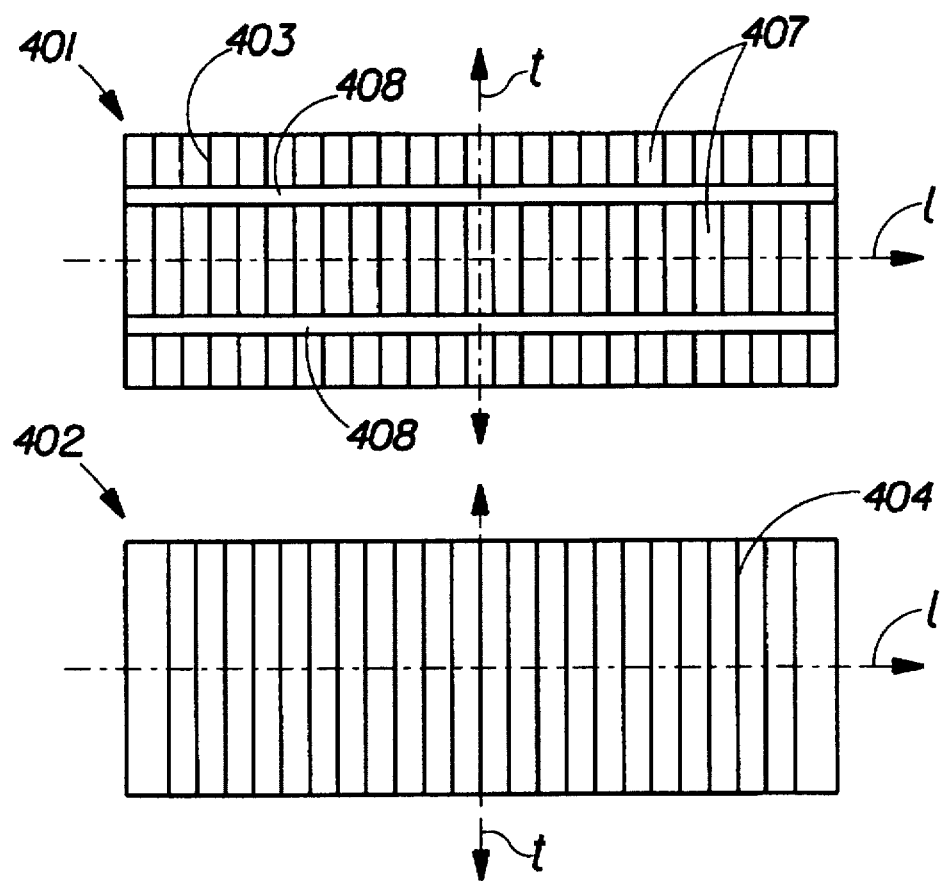
FIG. 33 is a plan view of the opposed meshing plates of the apparatus of FIG. 32 laid side-by-side with their meshing surfaces exposed.

Referring now to FIG. 33, it can be seen that plates 401 and 402 each have a longitudinal axis "l" and a transverse axis "t" which is substantially perpendicular to the longitudinal axis. Plate 401 includes toothed regions 407 and grooved regions 408 both which extend substantially parallel to the longitudinal axis of the plate 401. Within toothed regions 407 of plate 401 there are a plurality of teeth 403.

Plate 402 includes teeth 404 which mesh with teeth 403 of plate 401. When the base film 406 is formed between plates 401, 402 the portions of the base film 406 which are positioned within grooved regions 408 of plate 401 and teeth 404 on plate 402 remain undeformed. These regions correspond with the first regions 64 of web 52 shown in FIG. 5. The portions of the base film 406 positioned between toothed regions 407 of plate 401 and teeth 404 of plate 402 are incrementally and plastically formed creating rib-like elements 74 in the second regions 66 of web material 52.

Figure 34:
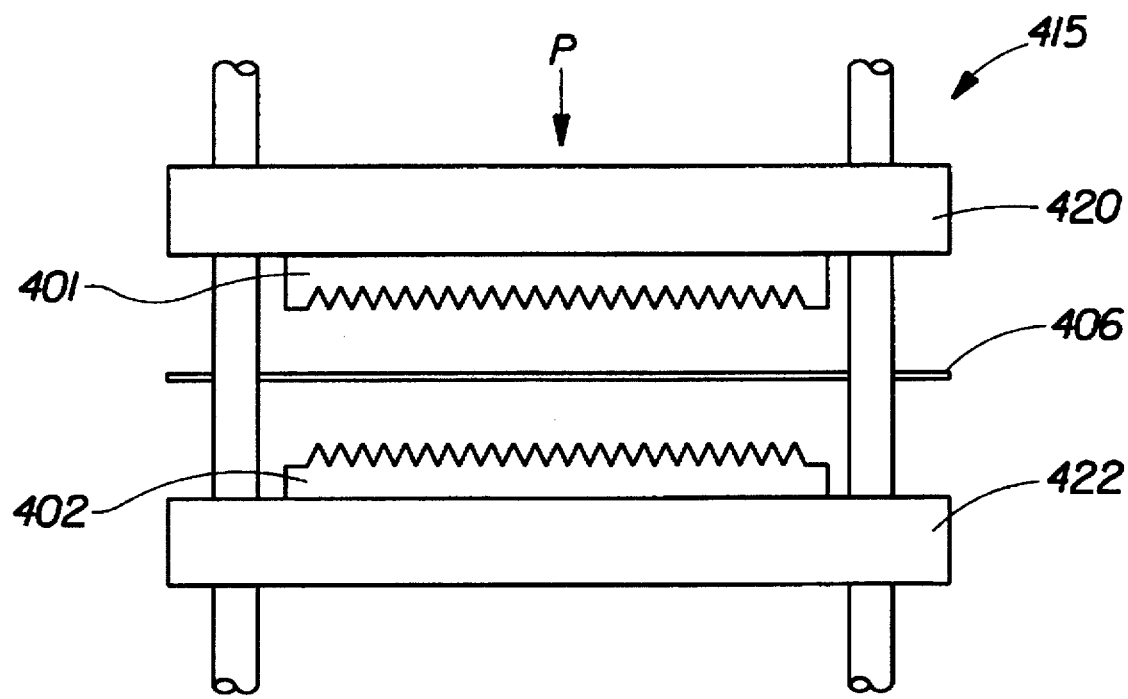
FIG. 34 is a simplified side elevational view of a static press used to form web materials of the present invention.

The method of formation can be accomplished in a static mode, where one discrete portion of a base film is deformed at a time. An example of such a method is shown in FIG. 34. A static press indicated generally as 415 includes an axially moveable plate or member 420 and a stationary plate 422. Plates 401 and 402 are attached to members 420 and 422, respectively. While plates 401 and 402 are separated, base film 406 is introduced between the plates, 401, 402. The plates are then brought together under a pressure indicated generally as "P". The upper plate 401 is then lifted axially away from plate 402 allowing the formed web material to be removed from between plates 401 and 402.

Figure 35:
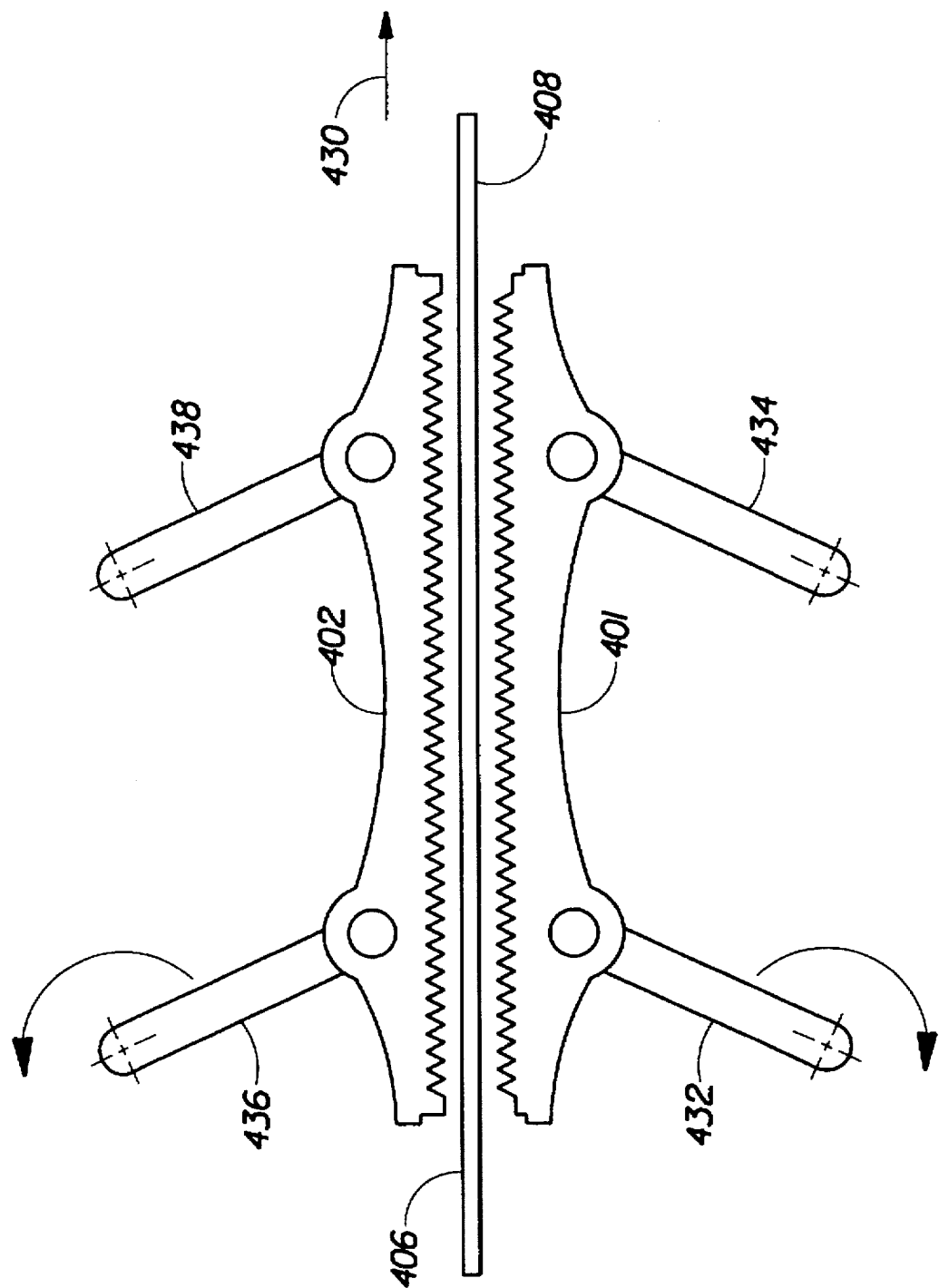
FIG. 35 is a simplified side elevational view of a continuous, dynamic press used to form web materials of the present invention.

FIG. 35 is an example of a continuous, dynamic press for intermittently contacting the moving web and forming a base material 406 into a formed web material of the present invention. Polymeric film 406 is fed between plates 401 and 402 in a direction generally indicated by arrow 430. Plate 401 is secured to a pair of rotatably mounted arms 432, 434 which travel in a clockwise direction which move plate 401 in a clockwise motion. Plate 402 is connected to a pair of rotary arms 436, 438 which travel in a counter clockwise direction moving plate 402 in a counter clockwise motion. Thus, as web 406 moves between plates 401 and 402 in direction indicated by arrow 430, a portion of the base film between the plates is formed and then released such that the plates 401 and 402 may come together and form another section of base film 406. This method has the benefit of allowing virtually any pattern of any complexity to be formed in a continuous process, e.g., uni-directional, bi-directional, and multi-directional patterns.

The dynamic press of FIG. 35 could be used on a completed absorbent article to from strainable networks into the completed product. For example, the entire completed absorbent article could be placed between plates 401 and 402 to create a strainable network in all layers of the absorbent article.

Another method of forming the base material into a web material of the present invention is vacuum forming. An example of a vacuum forming method is disclosed in commonly assigned U.S. Pat. No. 4,342,314, issued to Radel et al. on Aug. 3, 1982. Alternatively, the formed web material of the present invention may be hydraulically formed in accordance with the teachings of commonly assigned U.S. Pat. No. 4,609,518 issued to Curro et al. on Sep. 2, 1986. Each of the above said patents being incorporated herein by reference.

Figure 36:
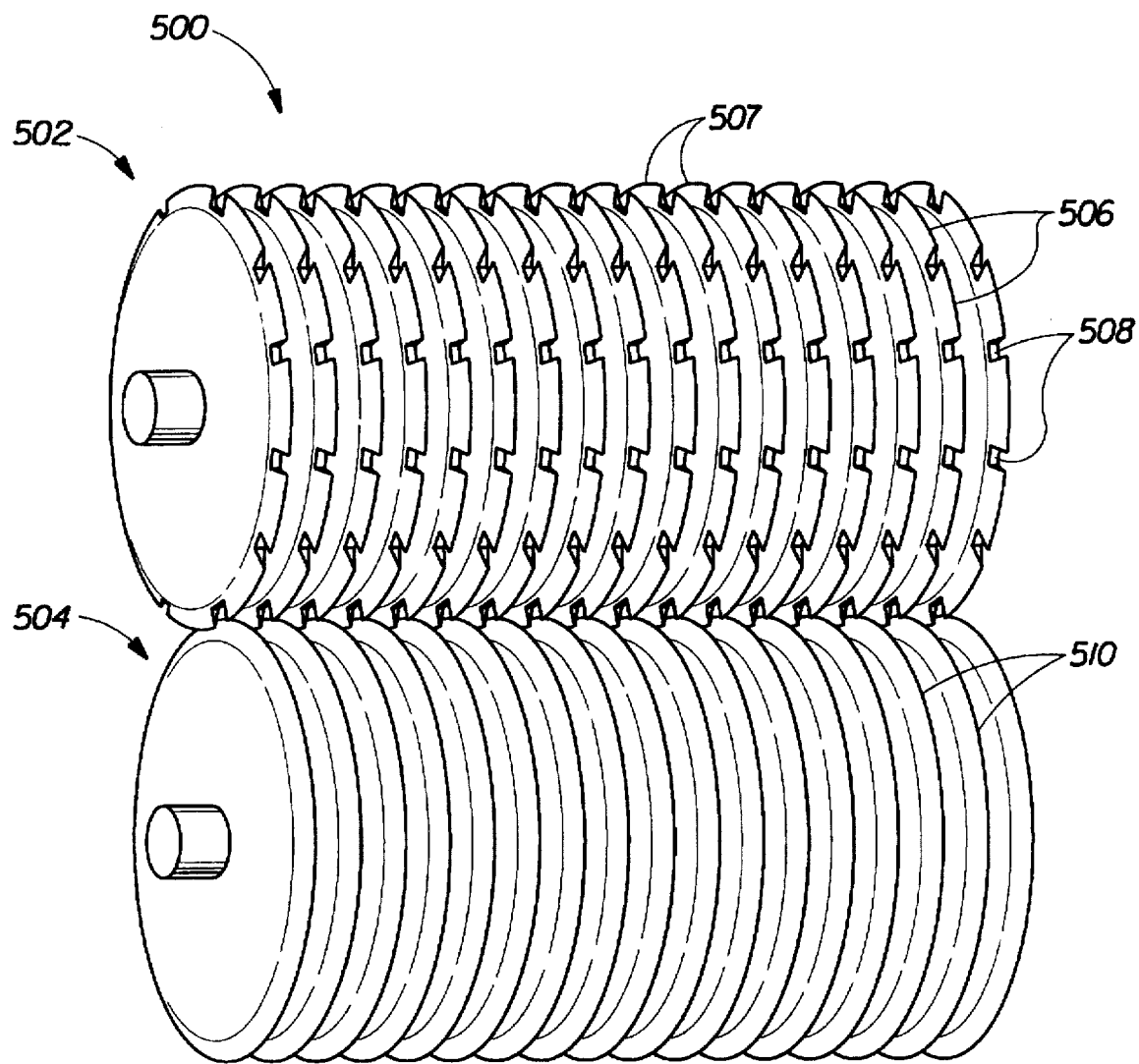
FIG. 36 is a simplified illustration of another apparatus used to form web materials of the present invention.

In FIG. 36 there is shown another apparatus generally indicated as 500 for forming the base film into a formed web material of the present invention. Apparatus 500 includes a pair of rolls 502, 504. Roll 502 includes a plurality of toothed regions 506 and a plurality of grooved regions 508 that extend substantially parallel to a longitudinal axis running through the center of the cylindrical roll 502. Toothed regions 506 include a plurality of teeth 507. Roll 504 includes a plurality of teeth 510 which mesh with teeth 507 on roll 502. As a base film is passed between intermeshing rolls 502 and 504, the grooved regions 508 will leave portions of the film unformed producing the first regions of the web material of the present invention. The portions of the film passing between toothed regions 506 and teeth 510 will be formed by teeth 507 and 510, respectively, producing rib-like elements in the second regions of the web material.

Alternatively, roll 504 may consist of a soft rubber. As the base film is passed between toothed roll 502 and rubber roll 504 the film is mechanically formed into the pattern provided by the toothed roll 502. The film within the grooved regions 508 will remain unformed, while the film within the toothed regions 506 will be formed producing rib-like elements of the second regions.

Figure 37:
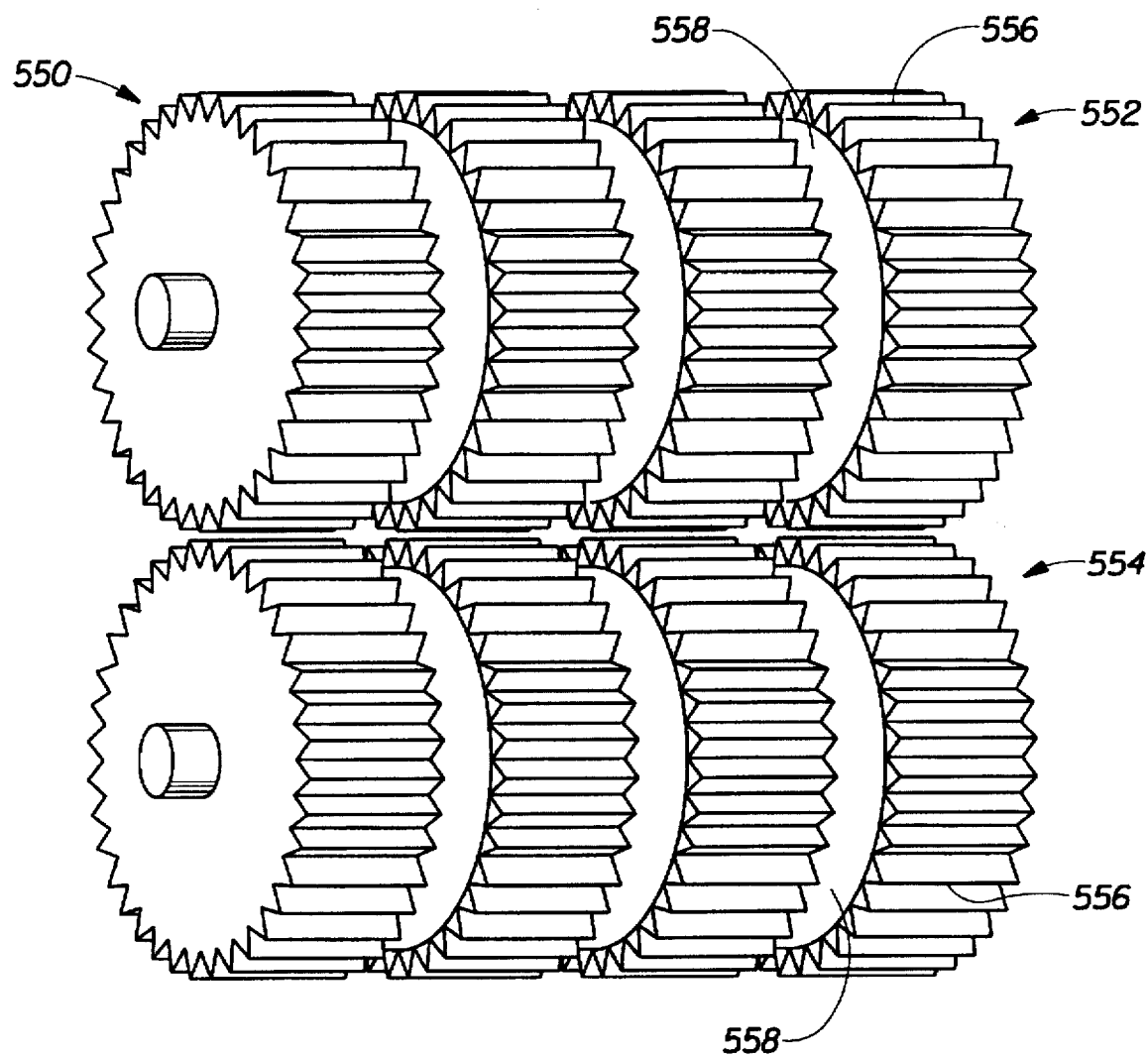
FIG. 37 is a simplified illustration of yet another apparatus used to form web materials of the present invention.

Referring now to FIG. 37, there is shown an alternative apparatus generally indicated as 550 for forming the based film into a formed web material in accordance with the teachings of the present invention. Apparatus 550 includes a pair of rolls 552, 554. Rolls 552 and 554 each have a plurality of toothed regions 556 and grooved regions 558 extending about the circumference of rolls 552, 554 respectively. As the base film passes between rolls 552 and 554, the grooved regions 558 will leave portions of the film uniformed, while the portions of the film passing between toothed regions 556 will be formed producing rib-like elements in second regions.

Web materials of the present invention may be comprised of polyolefins such as polyethylenes, including linear low density polyethylene (LLDPE), low density polyethylene (LDPE), ultra low density polyethylene (ULDPE), high density polyethylene (HDPE), or polypropylene and blends thereof with the above and other materials. Examples of other suitable polymeric materials which may also be used include, but are not limited to, polyester, polyurethanes, compostable or biodegradable polymers, heat shrink polymers, thermoplastic elastomers, metallocene catalyst-based polymers (e.g., INSITE® available from Dow Chemical Company and Exxact® available from Exxon), and breathable polymers. The web material may also be comprised of a synthetic woven, synthetic knit, nonwoven, apertured film, macroscopically expanded three-dimensional formed film, absorbent or fibrous absorbent material, foam, filled composition, or laminates and/or combinations thereof. The nonwovens may be made by but not limited to any of the following methods: spunlace, spunbond, meltblown, carded and/or air-through or calendar bonded, with a spunlace material with loosely bound fibers being the preferred embodiment.

While the present invention has been described as providing a web material from a single layer of base film, the present invention may be practiced equally well with other materials. While the fluid impervious polymeric film exhibiting an elastic-like behavior in the direction of applied elongation may be suitable for use a backsheet on a disposable diaper or sanitary napkin, such a web material would not function well as a topsheet on an absorbent article. Examples of other base materials from which the web of the present invention can be made and will function effectively as a fluid pervious topsheet on an absorbent article include two-dimensional apertured films and macroscopically expanded, three-dimensional, apertured formed films. Examples of macroscopically expanded, three-dimensional, apertured formed films are described in U.S. Pat. No. 3,929,135, issued to Thompson on Dec. 30, 1975; U.S. Pat. No. 4,324,246 issued to Mullane, et al. on Apr. 13, 1982; U.S. Pat. No. 4,342,314 issued to Radel, et al. on Aug. 3, 1982; U.S. Pat. No. 4,463,045 issued to Ahr, et al. on Jul. 31, 1984; and U.S. Pat. No. 5,006,394 issued to Baird on Apr. 9, 1991. Each of these patents are incorporated herein by reference.

Web materials of the present invention may include laminates of the above mentioned materials. Laminates may be combined by any number of bonding methods known to those skilled in the art. Such bonding methods include but are not limited to thermal bonding, adhesive bonding (using any of a number of adhesives including but not limited to spray adhesives, hot melt adhesives, latex based adhesives and the like), sonic bonding and extrusion laminating whereby a polymeric film is cast directly onto a substrate, and while still in a partially molten state, bonds to one side of the substrate, or by depositing meltblown fibers nonwoven directly onto a substrate.

The following are examples of specific embodiments of the present invention.

EXAMPLE 1

Two rigid plates similar to those of FIGS. 32 and 33 made by casting an aluminum filled epoxy material onto a machined metal mold were made. The outer dimensions of the plate are 5.0"×12"×0.75". On one surface of each plate are a series of "teeth" which are substantially triangular in cross section and measure 0.060" at these bases and taper to a vertex with a radius of 0.008" at the top. The centerlines of the teeth are spaced evenly and at 0.060" increments. The plates have matching holes and pins through their thickness to ensure consistent mating of the plates when they are brought together. On the "toothed" side of one plate a series of grooves are cut which are parallel to each other and perpendicular to the evenly spaced teeth. These grooves measure 0.065" in width and are continuous over the entire length of the plate, and are spaced at a distance of 0.50" on center. These grooves correspond to the undeformed regions of the deformed polymeric web.

A single thickness (0.001") of a polymeric film substantially comprised of LLDPE which was made via the melt casting method is placed between the two plates (one with grooves, one with only teeth). The plates with the film between them are placed in a hydraulic press with platens which are larger than the plates (to ensure that pressure is distributed evenly over the plates). At the edges of the plates are spacers which can vary in thickness to control the amount of interpenetration or "engagement" of the teeth. The plates are compressed between the platen of the press by a force of at least 4000 pounds which causes the regions of the film between the mating teeth of the plates to be formed. The film is left unformed in the regions corresponding to the grooves cut in one of the plates. The pressure is removed from the plates, and the formed web material is removed.

EXAMPLE 2

The plates described in Example 1 are used as described above. The material to be deformed is made from one layer of a carded calendar bonded polypropylene nonwoven which is laminated, using a spray adhesive such as 3M "Super 77 Spray Adhesive" (any number of hot melt or pressure sensitive adhesives could also be used), to a 1 mil thick cast polyethylene film. The nonwoven material is very easily formed in the cross direction. The laminate is placed between the two deformation plates such that the cross direction of the nonwoven is parallel to the grooves cut in the patterned plate. The resultant material has an improved aesthetic due to the lack of puckering upon release of the applied strain (such as that seen in the material of Example 1).

Test Methods

Surface-Pathlength

Pathlength measurements of formed material regions are to be determined by selecting and preparing representative samples of each distinct region and analyzing these samples by means of microscopic image analysis methods.

Samples are to be selected so as to be representative of each region's surface geometry. Generally, the transition regions should be avoided since they would normally contain features of both the first and second regions. The sample to be measured is cut and separated from the region of interest. The "measured edge" is to be cut parallel to a specified axis of elongation. Usually this axis is parallel to the formed primary-axis of either the first region or the second region. An unstrained sample length of one-half inch is to be "gauge marked" perpendicular to the "measured edge"; while attached to the web material, and then accurately cut and removed from the web material.

Measurement samples are then mounted onto the long-edge of a microscopic glass slide. The "measured edge" is to extend slightly (approximately 1 mm) outward from the slide edge. A thin layer of pressure-sensitive adhesive is applied to the glass face-edge to provide a suitable sample support means. For highly formed sample regions it has been found desirable to gently extend the sample in its axial direction (without imposing significant force) simultaneous to facilitate contact and attachment of the sample to the slide-edge. This allows improved edge identification during image analysis and avoids possible "crumpled" edge portions that require additional interpretation analysis.

Figure 38:
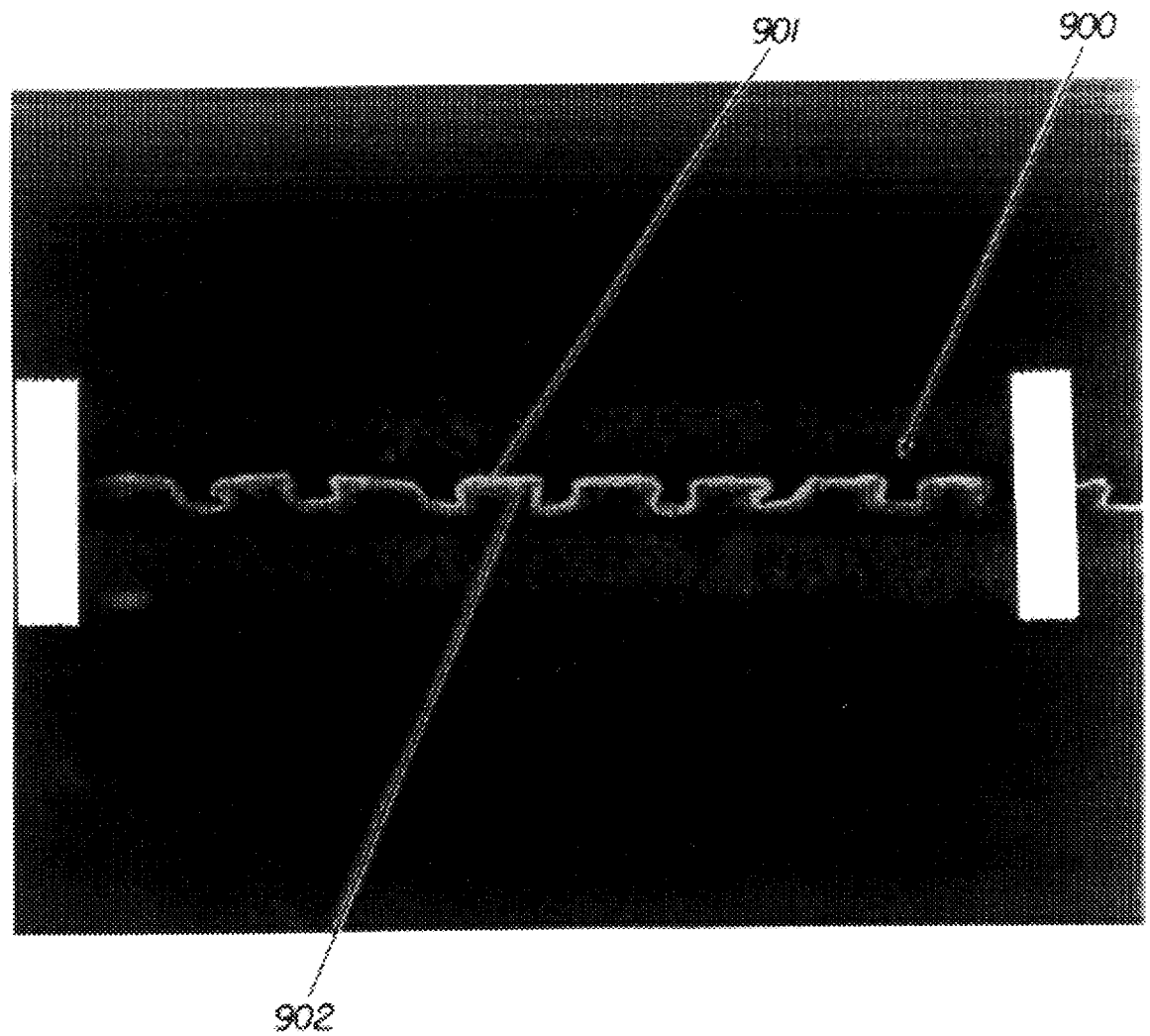
FIG. 38 is a photomicrograph of an "edge on" view of the second region used to determine the surface pathlength L2.

Images of each sample are to be obtained as "measured edge" views taken with the support slide "edge on" using suitable microscopic measuring means of sufficient quality and magnification. FIG. 38 shows a typical view of a portion of the second region of a sample 900 having a first side edge 901 and a second side edge 902 used to determine the surface-pathlength. Data herein presented was obtained using the following equipment. Keyence VH-6100 (20x Lens) video unit, with view-image prints made with a Sony Video printer Mavigraph unit. Video prints were image-scanned with a Hewlett Packard ScanJet IIP scanner. Image analysis was on a MacIntosh IICi computer utilizing the software NIH MAC Image version 1.45.

Using this equipment, a calibration image initially taken of a grid scale length of 0.500" with 0.005" increment-marks to be used for calibration setting of the computer image analysis program. All samples to be measured are then video-imaged and video-image printed. Next, all video-prints are image scanned at 100 dpi (256-level gray scale) into a suitable Mac image-file format. Finally, each image-file (including calibration file) is analyzed utilizing Mac Image 1.45 computer program. All samples are measured with freehanded line-measurement tool selected. Samples are measured on both side-edges and the lengths are recorded. Simple film-like (thin & constant thickness) samples require only one side-edge to be measured. Laminate and thick foam samples are measured on both side-edges. Length measurement tracings are to be made along the full gauge length of a cut sample. In cases of highly deformed samples, multiple (partially overlapping) images may be required to cover the entire cut sample. In these cases, select characteristic features common to both overlapping-images and utilize as "markers" to permit image length readings to adjoin but not overlap.

The final determination of surface-pathlength for each region is obtained by averaging the lengths of five (5) separate ½" gauge-samples of each region. Each gauge-sample "surface-pathlength" is to be the average of both side-edge surface-pathlengths.

While the test method described above is useful for many of the web materials of the present invention it is recognized that the test method may have to be modified to accommodate some of the more complex web materials within the scope of the present invention.

Poisson's Lateral Contraction Effect

The Poisson's lateral contraction effect is measured on an Instron Model 1122, as available from Instron Corporation of Canton, Mass., which is interfaced to a Gateway 2000 486/33 Hz computer available from Gateway 2000 N. Sioux City, S.Dak., using Test Works™ software which is available from Sintech, Inc. of Research Triangle Park, N.C. All essential parameters needed for testing are input in the TestWorks™ software for each test. Data collection is accomplished through a combination of manual sample width measurements, and elongation measurements made within TestWorks™.

The samples used for this test are 1" wide×4" long with the long axis of the sample cut parallel to the direction of the first region of the sample. The sample should be cut with a sharp knife or suitably sharp cutting device designed to cut a precise 1" wide sample. It is important that a "representative sample" should be cut so that an area representative of the symmetry of the overall pattern of the deformed regions is represented. There will be cases (due to variations in either the size of the deformed portion or the relative geometries of regions 1 and 2) in which it will be necessary to cut either larger or smaller samples that is suggested herein. In this case, it is very important to note (along with any data reported) the size of the sample, which are of the deformed region it was taken from and preferably include a schematic of the representative are used for the sample. In general, an "aspect ratio" of (2:1) for the actual extended tensile portion (l1:w1) is to be maintained if possible. Five samples are tested.

The grips of the Instron consist of air actuated grips designed to concentrate the entire griping force along a single line perpendicular to the direction of testing elongation having one flat surface and an opposing face from which protrudes a half round. No slippage should be permitted between the sample and the grips. The distance between the lines of gripping force should be 2" as measured by a steel rule held beside the grips. This distance will be referred to from here on as the "gauge length".

The sample is mounted in the grips with its long axis perpendicular to the direction of applied elongation. An area representative of the overall pattern geometry should be symmetrically centered between the grips. The crosshead speed is set to 10 in/min. The crosshead moves to the specified strain (measurements are made at both 20 and 60% elongation). The width of the sample at its narrowest point (w2) is measured to the nearest 0.02" using a steel rule. The elongation in the direction of applied extension is recorded to the nearest 0.02" on the TestWorks software. The Poisson's Lateral Contraction Effect (PLCE) is calculated using the following formula $$PLCE = \frac{\frac{|w2 - w1|}{w1}}{\frac{|l2 - l1|}{l1}}$$

where w2=The width of the sample under an applied longitudinal elongation;

w1=The original width of the sample;

l2=The length of the sample under an applied longitudinal elongation; and l1=The original length of the sample (gauge length);

Measurements are made at both 20 and 60% elongation using five different samples for each given elongation. The PLCE at a given percent elongation is the average of five measurements.

While the test method described above is useful for many of the web materials of the present invention it is recognized that the test method may have to be modified to accommodate some of the more complex web materials within the scope of the present invention.

Hysteresis Test

The hysteresis test is used for measuring the percent set and percent force relaxation of a material. The tests are performed on an Instron Model 1122, available from Instron Corporation of Canton, Mass. which is interfaced to a Gateway 2000 486/33 Hz computer available from Gateway 2000 of N. Sioux City, S.Dak. 57049, using TestWorks™ software which is available from Sintech, Inc. of Research Triangle Park, N.C. 27709. All essential parameters needed for testing are input in the TestWorks™ software for each test (i.e. Crosshead Speed, Maximum percent elongation Point and Hold Times). Also, all data collection, data analysis and graphing are done using the TestWorks™ software.

The samples used for this test are 1" wide×4" long with the long axis of the sample cut parallel to the direction of maximum extensibility of the sample. The sample should be cut with a sharp exacto knife or some suitably sharp cutting device design to cut a precise 1" wide sample. (If there is more than one direction of elongation of the material, samples should be taken parallel to representative directions of elongation). The sample should be cut so that an area representative of the symmetry of the overall pattern of the deformed region is represented. There will be cases (due to variations in either the size of the deformed portion or the relative geometries of the first and second regions) in which it will be necessary to cut either larger or smaller samples than is suggested herein. In this case, it is very important to note (along with any data reported) the size of the sample, which area of the deformed region it was taken from and preferably include a schematic of the representative area used for the sample. Three separate tests at 20, 60 and 100% strain are typically measured for each material. Three samples of a given material are tested at each percent elongation.

The grips of the Instron consist of air actuated grips designed to concentrate the entire gripping force along a single line perpendicular to the direction of testing stress having one flat surface and an opposing face from which protrudes a half round to minimize slippage of the sample. The distance between the lines of gripping force should be 2" as measured by a steel rule held beside the grips. This distance will be referred to from hereon as the "gauge length". The sample is mounted in the grips with its long axis perpendicular to the direction of applied percent elongation. The crosshead speed is set to 10 in/min. The crosshead moves to the specified maximum percent elongation and holds the sample at this percent elongation for 30 seconds. After the thirty seconds the crosshead returns to its original position (0% elongation) and remains in this position for 60 seconds. The crosshead then returns to the same maximum percent elongation as was used in the first cycle, holds for thirty seconds and then again returns to zero.

A graph of two cycles is generated. A representative graph is shown in FIG. 7. The percent force relaxation is determined by the following calculation of the force data from the first cycle:

$$\frac{\text{Force at Max. \% elongation} - \text{Force after 30 sec. hold} \times 100}{\text{Force at Maximum \% elongation (cycle 1)}} = \% \text{ Force Relaxation}$$

The percent set is the percent elongation of the sample of the second cycle where the sample starts to resist the elongation. The percent set and the percent force relaxation are shown graphically also in FIGS. 7, 9, 11, 13 and 15. The average percent force relaxation and percent set for three samples is reported for each maximum percent elongation value tested.

While the test method described above is useful for many of the web materials of the present invention it is recognized that the test method may have to be modified to accommodate some of the more complex web materials within the scope of the present invention.

Tensile Test

The tensile test is used for measuring force versus percent elongation properties and percent available stretch of a material. The tests are performed on an Instron Model 1122, available from Instron Corporation of Canton, Mass. which is interfaced to a Gateway 2000 486/33 Hz computer available from Gateway 2000 N. Sioux City, S.Dak., using TestWorks™ software which is available from Sintech, Inc. of Research Triangle Park, N.C. All essential parameters needed for testing are input in the TestWorks™ software for each test. Also, all data collection, data analysis and graphing are done using the TestWorks™ software.

The samples used for this test are 1" wide×4" long with the long axis of the sample cut parallel to the direction of maximum extensibility of the sample. The sample should be cut with a sharp exacto knife or some suitably sharp cutting device design to cut a precise 1" wide sample. (If there is more than one direction of extensibility of the material, samples should be taken parallel to representative direction of elongation). The sample should be cut so that an area representative of the symmetry of the overall pattern of the deformed region is represented. There will be cases (due to variation in either the size of the deformed portion or the relative geometries of regions 1 and 2) in which it will be necessary to cut either larger or smaller samples than is suggested herein. In this case, it is very important to note (along with any data reported) the size of the sample, which area of the deformed region it was taken from and preferably include a schematic of the representative area used for the sample. Three samples of a given material are tested.

The grips of the Instron consist of air actuated grips designed to concentrate the entire gripping force along a single line perpendicular to the direction of testing stress having one flat surface and an opposing face from which protrudes a half round to minimize slippage of the sample. The distance between the lines of gripping force should be 2" as measured by a steel rule held beside the grips. This distance will be referred to from hereon as the "gauge length". The sample is mounted in the grips with its long axis perpendicular to the direction of applied percent elongation. The crosshead speed is set to 10 in/min. The crosshead elongates the sample until the sample breaks at which point the crosshead stops and returns to its original position (0% elongation).

Graphs of the tensile data are shown in FIGS. 6, 8, 10, 12 and 14. The percent available stretch is the point at which there is an inflection in the force—elongation curve, beyond which point there is a rapid increase in the amount of force required to elongate the sample further. This point is shown graphically in FIGS. 6, 8, 10, 12 and 14. The average of the percent available stretch for three samples is recorded.

While the test method described above is useful for many of the web materials of the present invention it is recognized that the test method may have to be modified to accommodate some of the more complex web materials within the scope of the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modification that are within the scope of this invention.

What is claimed is:

1. A method for forming a web material into a web material exhibiting an elastic-like behavior in response to an applied elongation along at least one axis thereof, said web material comprising a strainable network having first and second regions, said first region providing a first, elastic-like resistive force to the applied elongation, and the second region providing a second resistive force to further applied elongation, said method comprising the steps of:

a) providing a web material; and b) feeding said web material between a first roll and a second roll, said first roll comprising a plurality of toothed regions spaced apart by a plurality of grooved regions, said toothed regions comprising a plurality of teeth, said second roll comprising a plurality of teeth which mesh with said teeth on said first roll, as said web material is fed between said first roll and said second roll the portion of said web material passing between the teeth on said first roll and the teeth on said second roll being formed into said second regions of said web material while the portion of said web material passing between the grooves on said first roll and the teeth on said second roll being formed into said first regions of said web material.

* * * * *

UNITED STATES PATENT AND TRADEMARK OFFICE
CERTIFICATE OF CORRECTION

PATENT NO. : 5,723,087
DATED : March 3, 1998
INVENTOR(S) : Charles W. Chappell, et al.

It is certified that error appears in the above-identified patent and that said Letters Patent is hereby corrected as shown below:

Column 6, line 59, delete "composed" and insert therefor -- composted --.

Column 7, line 47, delete "content" and insert therefor -- context --.

Column 8, line 12, delete "of" and insert therefor -- for --.

Column 8, line 48, delete "of" and insert therefor -- or --.

Column 13, line 1, delete "of" and insert therefor -- for --.

Column 13, line 37, delete "think" and insert therefor -- thin --.

Column 20, line 42, delete "from" and insert therefor -- form --.

Column 21, line 16, delete "based" and insert therefor -- base --.

Column 21, line 24, delete "uniformed," and insert therefor -- unformed, --.

Column 22, line 25, delete "these" and insert therefor -- their --.

Column 22, line 46, delete "platen" and insert therefor -- platens --.

Column 23, line 53, delete "freehanded" and insert therefor -- freehand --.

Column 24, line 27, delete "regions" and insert therefor -- region --.

Column 24, line 33, delete "are" and insert therefor -- area --.

Column 24, line 35, delete "are" and insert therefor -- area --.

Column 24, line 40, delete "griping" and insert therefor -- gripping --.

UNITED STATES PATENT AND TRADEMARK OFFICE
CERTIFICATE OF CORRECTION

PATENT NO. : 5,723,087
DATED : March 3, 1998
INVENTOR(S) : Charles W. Chappell, et al.

It is certified that error appears in the above-identified patent and that said Letters Patent is hereby corrected as shown below:

Column 27, line 16, delete "modification" and insert therefor -- modifications --.

Signed and Sealed this

Nineteenth Day of September, 2000

Attest:

Q. TODD DICKINSON

*Attesting Officer*  *Director of Patents and Trademarks*